(12) United States Patent
Darna

(10) Patent No.: US 10,238,575 B2
(45) Date of Patent: Mar. 26, 2019

(54) THERAPEUTIC SUBSTANCE AND ACUPRESSURE SYSTEM

(71) Applicant: Jacqueline Cecilia Darna, Tampa, FL (US)

(72) Inventor: Jacqueline Cecilia Darna, Tampa, FL (US)

( * ) Notice: Subject to any disclaimer, the term of this patent is extended or adjusted under 35 U.S.C. 154(b) by 617 days.

(21) Appl. No.: 14/590,637

(22) Filed: Jan. 6, 2015

(65) Prior Publication Data

US 2015/0224025 A1 Aug. 13, 2015

Related U.S. Application Data

(60) Provisional application No. 61/964,502, filed on Jan. 7, 2014.

(51) Int. Cl.
*A61B 17/00* (2006.01)
*A61H 39/04* (2006.01)
*A61M 21/00* (2006.01)

(52) U.S. Cl.
CPC ......... *A61H 39/04* (2013.01); *A61H 2201/10* (2013.01); *A61M 2021/0016* (2013.01); *A61M 2209/088* (2013.01)

(58) Field of Classification Search
CPC .. A61H 39/04; A61H 2201/10; A44C 15/002; A61M 2021/0016; A61M 2209/088
See application file for complete search history.

(56) References Cited

U.S. PATENT DOCUMENTS

| | | | |
|---|---|---|---|
| 4,713,291 A * | 12/1987 | Sasaki | D01D 5/24 264/172.15 |
| 5,405,357 A | 4/1995 | Rowe-Lanzisera et al. | |
| 6,299,586 B1 | 10/2001 | Cao | |
| 7,186,260 B2 * | 3/2007 | Hyson | A61L 15/44 602/48 |
| 2006/0182704 A1 * | 8/2006 | Gianelli | A45D 44/002 424/70.14 |
| 2007/0241482 A1 * | 10/2007 | Giller | G03G 15/224 264/494 |
| 2013/0204293 A1 | 8/2013 | Sakakibara | |
| 2014/0193764 A1 | 7/2014 | Pizzini | |
| 2014/0257155 A1 * | 9/2014 | Altinok | A61H 39/04 602/1 |

FOREIGN PATENT DOCUMENTS

| | | |
|---|---|---|
| JP | 2012030018 A * | 2/2012 |
| WO | 00/16752 A2 | 3/2000 |
| WO | 2007/073106 A1 | 6/2007 |
| WO | 2013/043581 A1 | 3/2013 |

OTHER PUBLICATIONS http://www.skeptics.org.nz/SK:VIEWARTICLE::waDeptTOC.1,A761, Bands of Hope, New Zealand Skeptics, 1992/1993.
http://hamptonroads.com/2012/04/it%E2%80%99s-all-wrist-are-%E2%80%9Cjasmine-w, Quick Tips for Wellness, HamptonRoads. com, Apr. 27, 2012.
http://nomonausea.com/.
Reliefband® 2.0, https://www.reliefband.com/collections/reliefband/products/reliefband%C2%AE-2-0.

* cited by examiner

*Primary Examiner* — Gregory Anderson
(74) *Attorney, Agent, or Firm* — Akerman LLP; Mark D. Passler; Brice S. Dumais

(57) ABSTRACT

According to one embodiment, a system includes an acupressure device configured to apply pressure to one or more pressure points on a mammal. The system further includes a therapeutic substance coupled to the acupressure device.

8 Claims, 15 Drawing Sheets

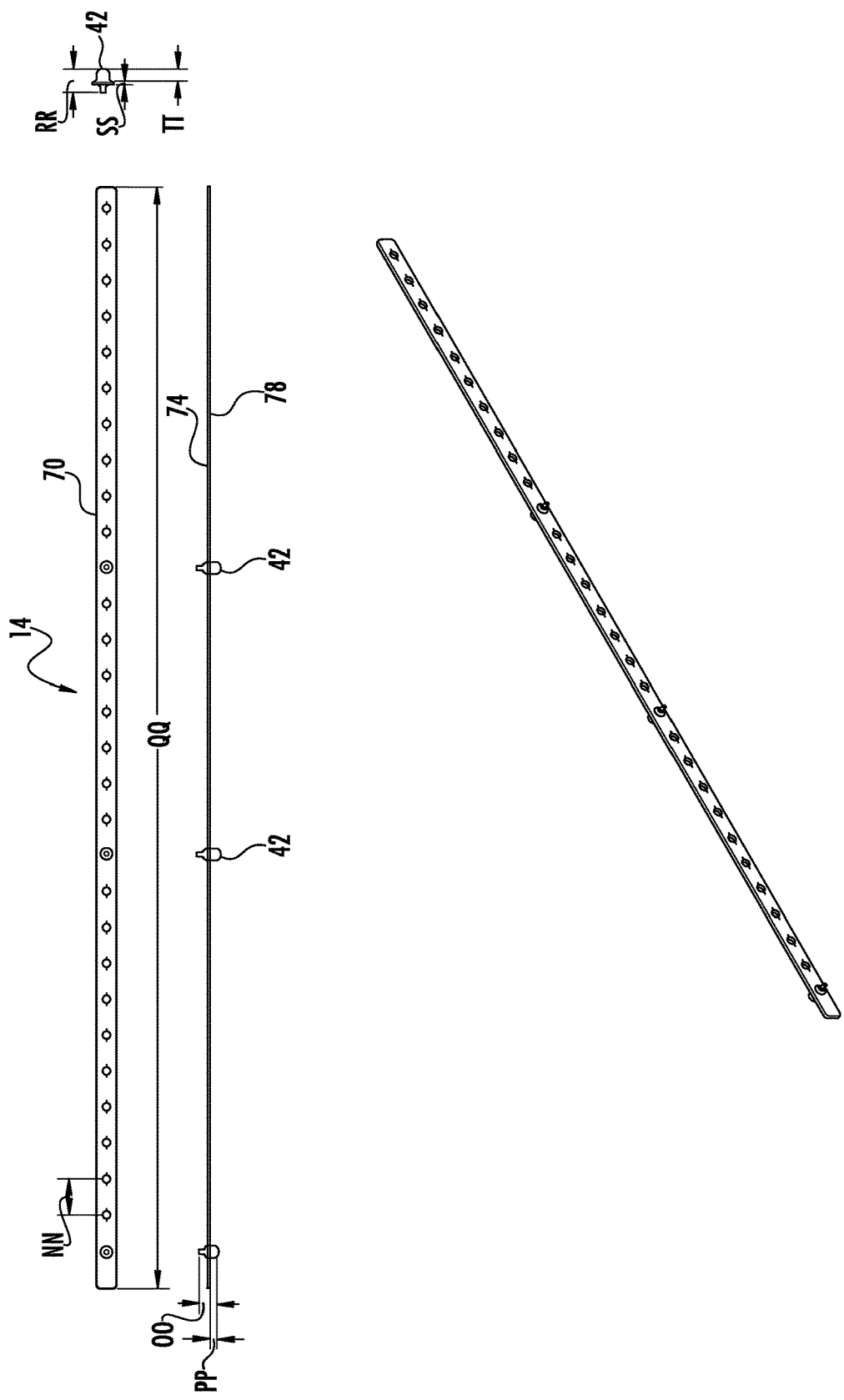

THERAPEUTIC SUBSTANCE AND ACUPRESSURE SYSTEM

CROSS-REFERENCE TO RELATED APPLICATION

This application claims priority to U.S. Provisional Patent Application No. 61/964,502, filed Jan. 7, 2014, the entirety of which is incorporated herein.

TECHNICAL FIELD

This disclosure relates generally to the field of therapeutic devices and more specifically to a therapeutic substance and acupressure system.

BACKGROUND

Traditionally, holistic and/or non-western health practices have been used as alternatives to conventional health/medical methodology. Examples of such traditional holistic and/or non-western health practices include acupuncture, acupressure, and aromatherapy. Traditionally, such techniques are used individually to provide therapy to a patient and/or such techniques traditionally require a trained practitioner in order to be performed on a patient. This use of such traditional techniques, however, may be deficient.

SUMMARY

According to one embodiment, a system includes an acupressure device configured to apply pressure to one or more pressure points on a mammal. The system further includes a therapeutic substance coupled to the acupressure device.

Certain embodiments of the disclosure may provide one or more technical advantages. For example, the system includes an acupressure device and a therapeutic substance coupled to the acupressure device. In particular embodiments, by coupling the therapeutic substance to the acupressure device, a mammal using the system may receive therapy from the system from both the acupressure device and the therapeutic substance. Furthermore, in particular embodiments, the therapeutic substance may provide a more rapid therapeutic benefit to the mammal while the acupressure device may provide a more delayed, but potentially longer, therapeutic benefit. Additionally, in particular embodiments, the system may allow the mammal to receive one or more therapeutic benefits no matter where the mammal is located (such as in the car, in an airplane, at the beach, in the water, in the hospital, etc.) and/or no matter what the mammal is doing (such as working, exercising, swimming, attending school classes, etc.). Also, in particular embodiments, the system may provide a safe, accurate, convenient, and/or cost-effective manner of providing one or more benefits to a mammal via acupressure and aromatherapy.

Certain embodiments of the disclosure may include none, some, or all of the above technical advantages. One or more other technical advantages may be readily apparent to one skilled in the art from the figures, descriptions, and claims included herein.

BRIEF DESCRIPTION OF THE FIGURES

For a more complete understanding of the present disclosure and its features and advantages, reference is now made to the following description, taken in conjunction with the accompanying drawings, in which:

FIGS. 3a-3e illustrate examples of an acupressure device of FIG. 1; and

DETAILED DESCRIPTION

Embodiments of the present disclosure are best understood by referring to FIGS. 1-4 of the drawings, like numerals being used for like and corresponding parts of the various drawings.

Figure 1:
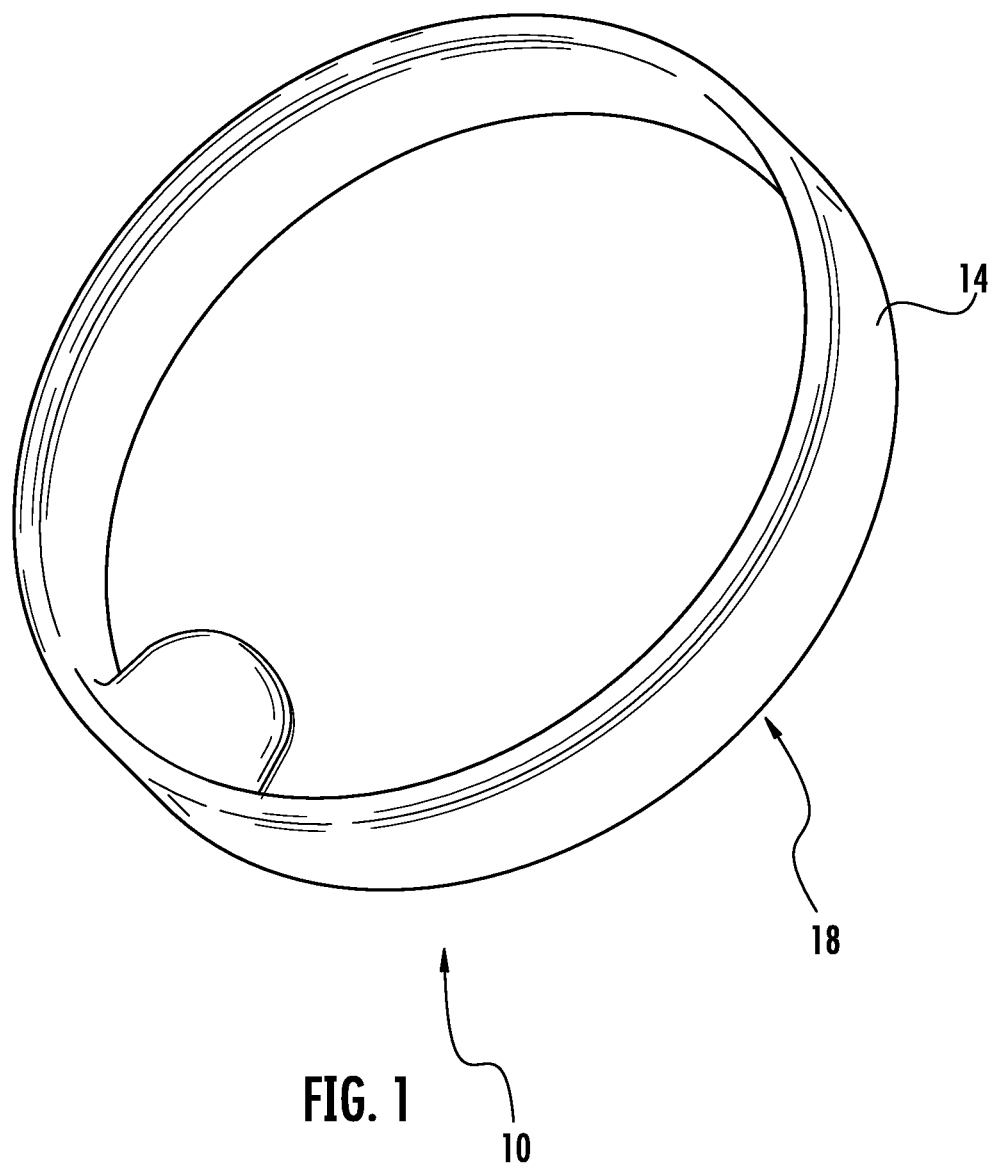
FIG. 1 illustrates an example therapeutic substance and acupressure system.

FIG. 1 illustrates an example therapeutic substance and acupressure system. As illustrated, the therapeutic substance and acupressure system 10 includes an acupressure device 14 and a therapeutic substance 18 coupled to the acupressure device 14. The acupressure device 14 may be configured to apply pressure to one or more pressure points on a mammal (such as an adult human, a child human, a dog, a cat, a horse, or any other mammal). The therapeutic substance 18 may be configured to provide one or more beneficial effects on the body and/or mind of the mammal. In particular embodiments, by coupling the therapeutic substance 18 to the acupressure device 14, a mammal using the system 10 may receive therapy from both the acupressure device 14 and the therapeutic substance 18. Furthermore, in particular embodiments, the therapeutic substance 18 may provide a more rapid therapeutic benefit to the mammal while the acupressure device 14 may provide a more delayed, but potentially longer, therapeutic benefit. Additionally, in particular embodiments, the system 10 may allow the mammal to receive one or more therapeutic benefits no matter where the mammal is located (such as in the car, in an airplane, at the beach, in the water, in the hospital, etc.) and/or no matter what the mammal is doing (such as working, exercising, swimming, attending school classes, etc.). Also, in particular embodiments, the system 10 may provide a safe, accurate, convenient, and/or cost-effective manner of providing one or more benefits to a mammal via acupressure and aromatherapy.

Traditionally, holistic and/or non-western health practices have been used as alternatives to conventional health/medical methodology. Examples of such traditional holistic and/or non-western health practices include acupuncture, acupressure, and aromatherapy. Acupuncture consists of inserting various small, thin needles into a person's skin at certain locations on the body. There are more than one thousand pre-mapped locations on the human body and the locations are chosen based on the ailment or condition a person is experiencing. By inserting the needles, a person's chi, or life-force, can be manipulated. Unfortunately, acupuncture is traditionally performed by a trained acupuncturist, thereby preventing a patient from receiving treatment at any time they desire. Furthermore, many people may be afraid of needles, preventing them from ever considering acupuncture.

Acupressure (and other pressure-applied therapies) is similar to acupuncture, but it is non-invasive. Instead of inserting needles, a person may have pressure applied (constantly or periodically) at certain locations on their body. Due to the pressure at certain locations, the person's body may elicit a biochemical response (such as creating hormones) to create a medicinal therapeutic value (such as to decrease nausea, for example). In acupressure, one or more acupressure devices may be attached to a person's skin in order to provide the pressure. Such devices may allow greater control over the amount of pressure that is applied, and may prevent the person from having to go to a trained acupuncturist. Unfortunately, in acupressure, the response time for therapy may be delayed, as the pressure may need to be applied for a long period of time before relief occurs. Furthermore, traditional acupressure devices tend to be either tedious or unattractive.

Aromatherapy involves the use of aromatic oils to elicit quick (such as instantaneous) results to medically relevant problems. Traditionally, aromatherapy is effectuated by the addition of an aromatic material to massage oil, bath oil, candle wax, pillow stuffing, a vaporizing device, or a diffusing device. These traditional methods of aromatherapy, however, are time consuming, cumbersome, messy, and/or require the presence either of an attendant masseuse or of a piece of non-portable equipment.

Contrary to such typical deficiencies of acupuncture, acupressure, and aromatherapy, the therapeutic substance and acupressure system 10 of FIG. 1 may provide one or more advantages. For example, as illustrated, the system 10 includes an acupressure device 14 and a therapeutic substance 18 coupled to the acupressure device 14. In particular embodiments, by coupling the therapeutic substance 18 to the acupressure device 14, a mammal using the system 10 may receive therapy from both the acupressure device 14 and the therapeutic substance 18. Furthermore, in particular embodiments, the therapeutic substance 18 may provide a more rapid therapeutic benefit to the mammal while the acupressure device 14 may provide a more delayed, but potentially longer, therapeutic benefit. Additionally, in particular embodiments, the system 10 may allow the mammal to receive one or more therapeutic benefits no matter where the mammal is located (such as in the car, in an airplane, at the beach, in the water, in the hospital, etc.) and/or no matter what the mammal is doing (such as working, exercising, swimming, attending school classes, etc.). Also, in particular embodiments, the system 10 may provide a safe, accurate, convenient, and/or cost-effective manner of providing one or more benefits to a mammal via acupressure and aromatherapy.

As illustrated, FIG. 1 includes an acupressure device 14. The acupressure device 14 may include any device configured to apply pressure to one or more pressure points on a mammal (such as an adult human, a child human, a dog, a cat, a horse, or any other mammal). The acupressure device 14 may have any form, type, or shape. For example, the acupressure device 14 may be a wrist band, an appendage band (such as a band that is positioned on a mammal's arm, leg, or any other appendage), a head band, a sticker (or patch) that may be applied to the skin (or fur or hair) of a mammal, a belt, a brace, a pressure-applying garment (such as a shirt, leggings, etc.), a clip (such as a hand clip placed in the wedge between a person's fingers), a ring, any other form, type, or shape of a device, or any combination of the preceding. Examples of forms, types, or shapes of an acupressure device 14 are discussed below in further detail with regard to FIGS. 3a-3e. In particular embodiments, the acupressure device 14 may be a commercially known (or commercially available) device that may be altered, modified, and/or enhanced in accordance with one or more embodiments of this disclosure.

Figure 2A:
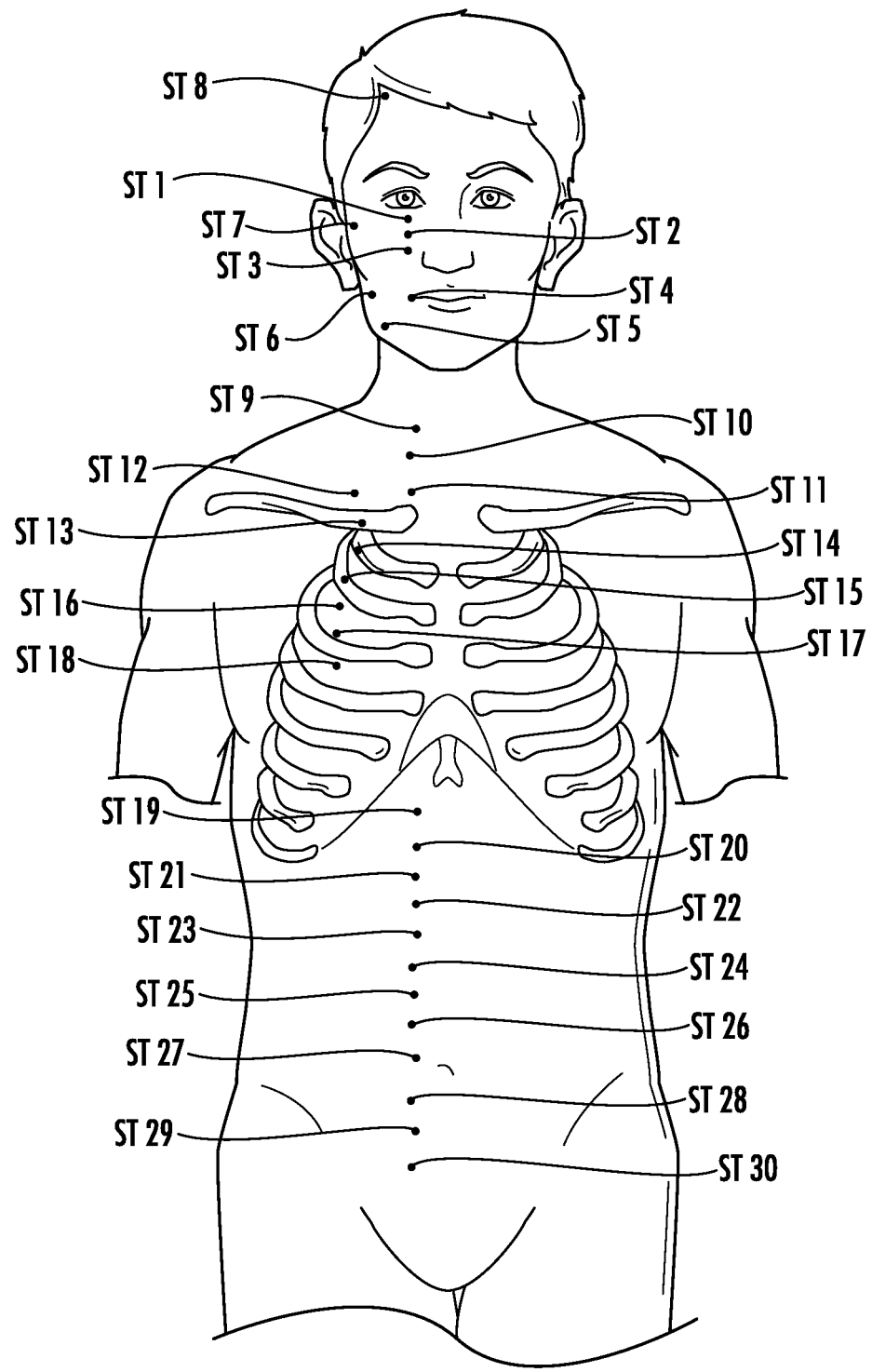
FIGS. 2a-2h illustrate the location of example pressure points of a mammal.
Figure 2B:
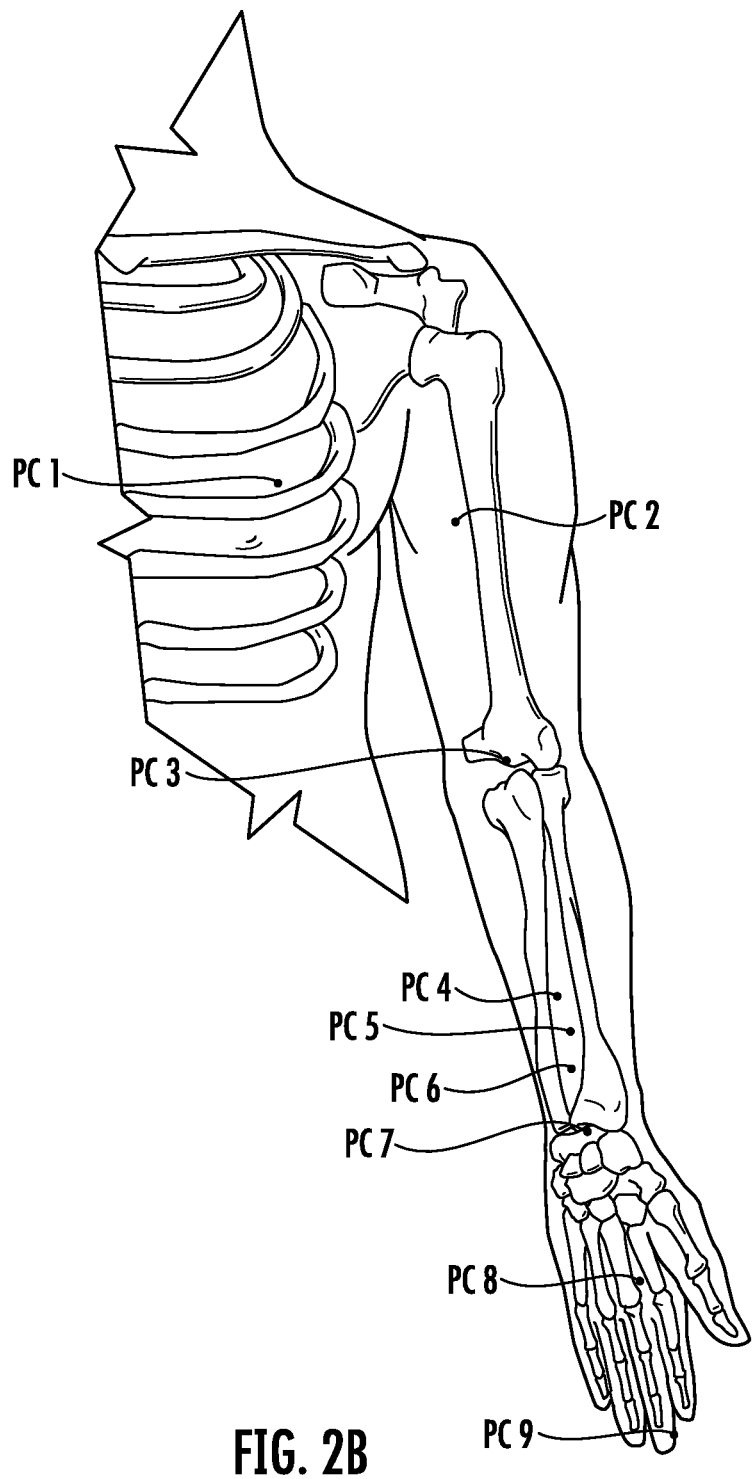
Figure 2C:
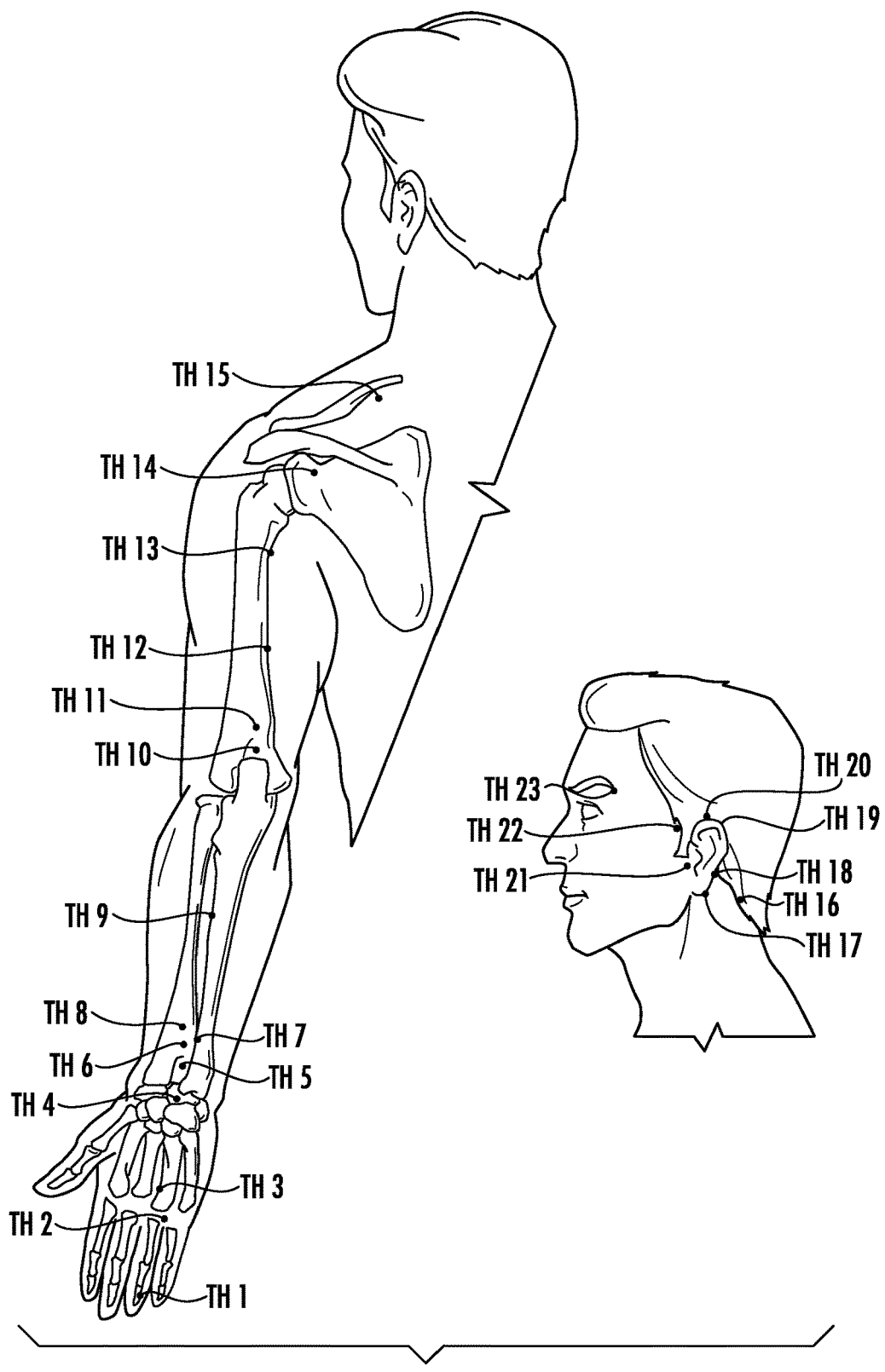
Figure 2D:
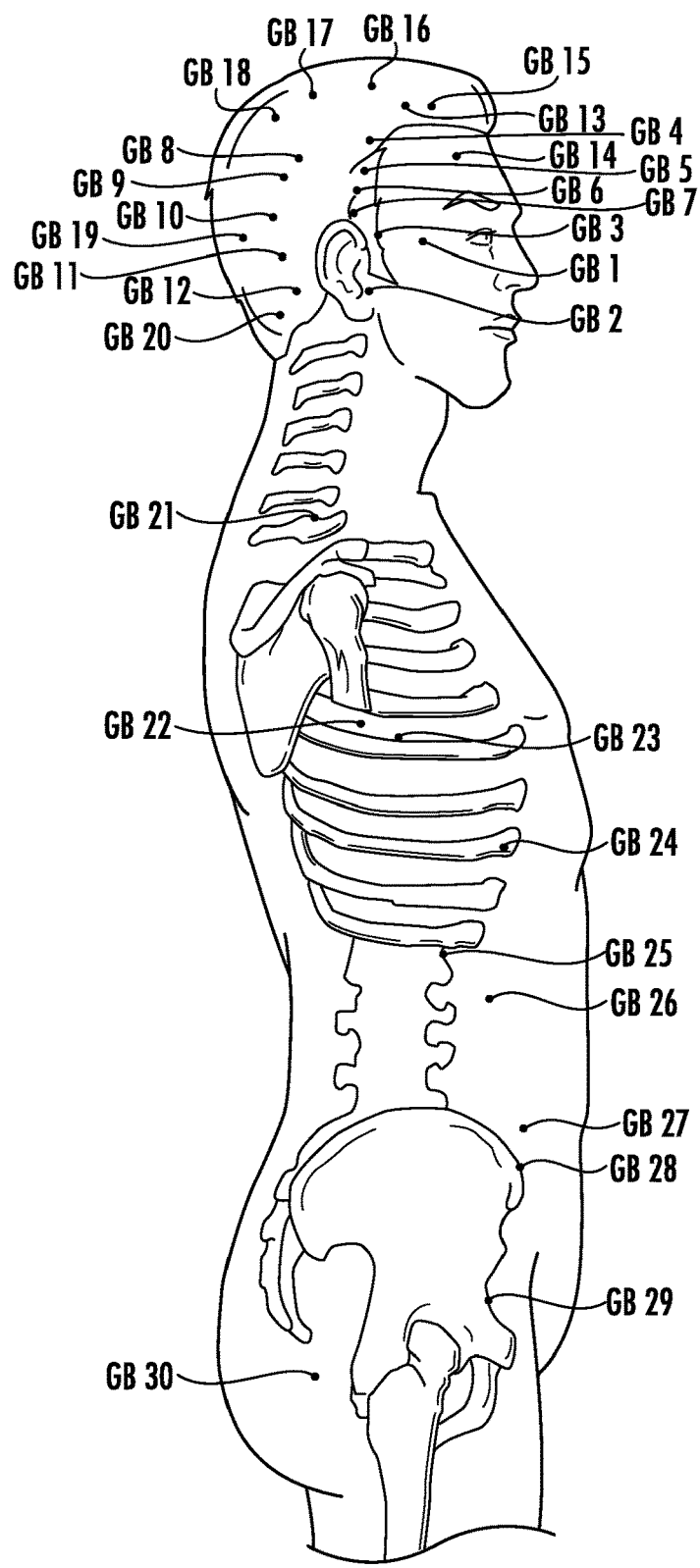
Figure 2E:
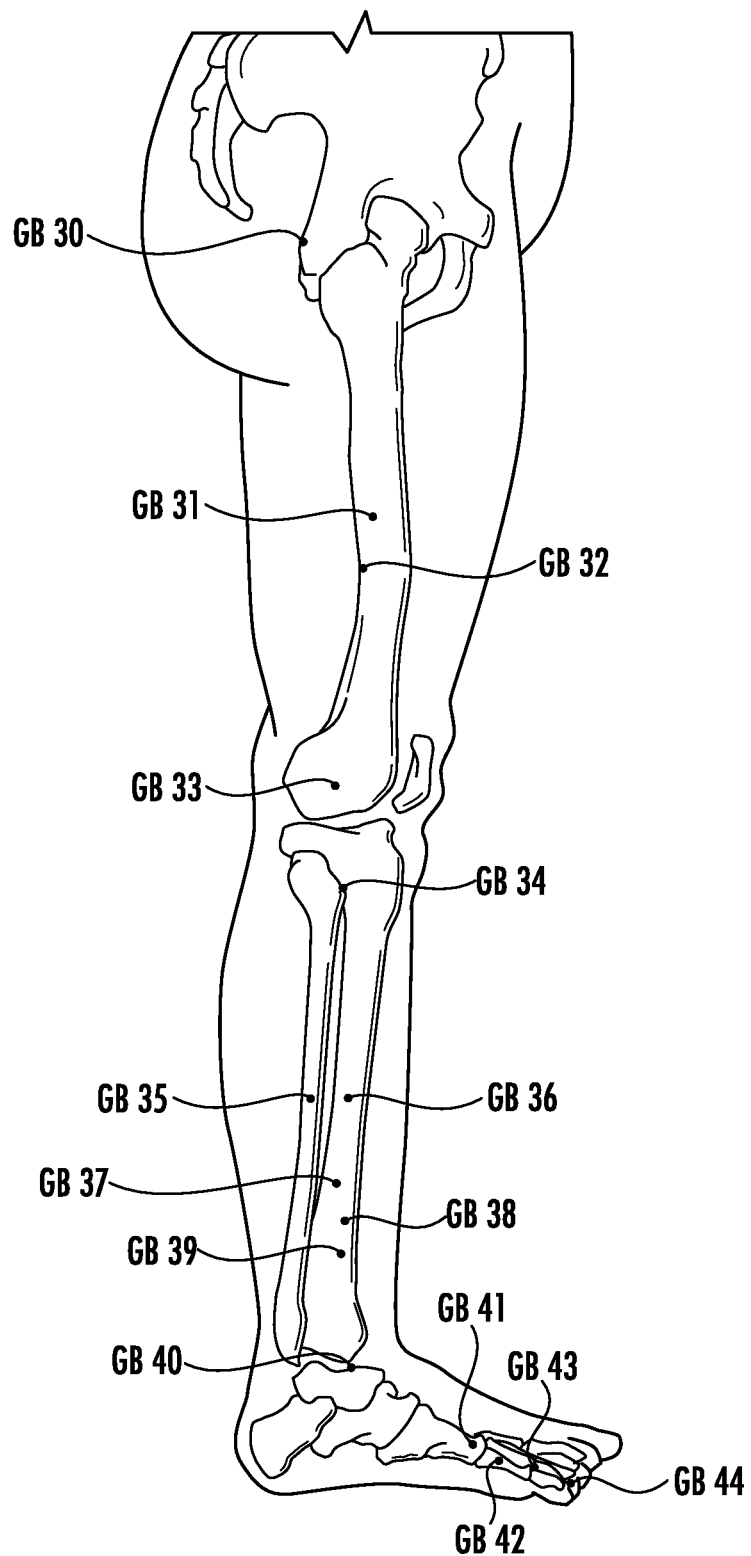
Figure 2F:
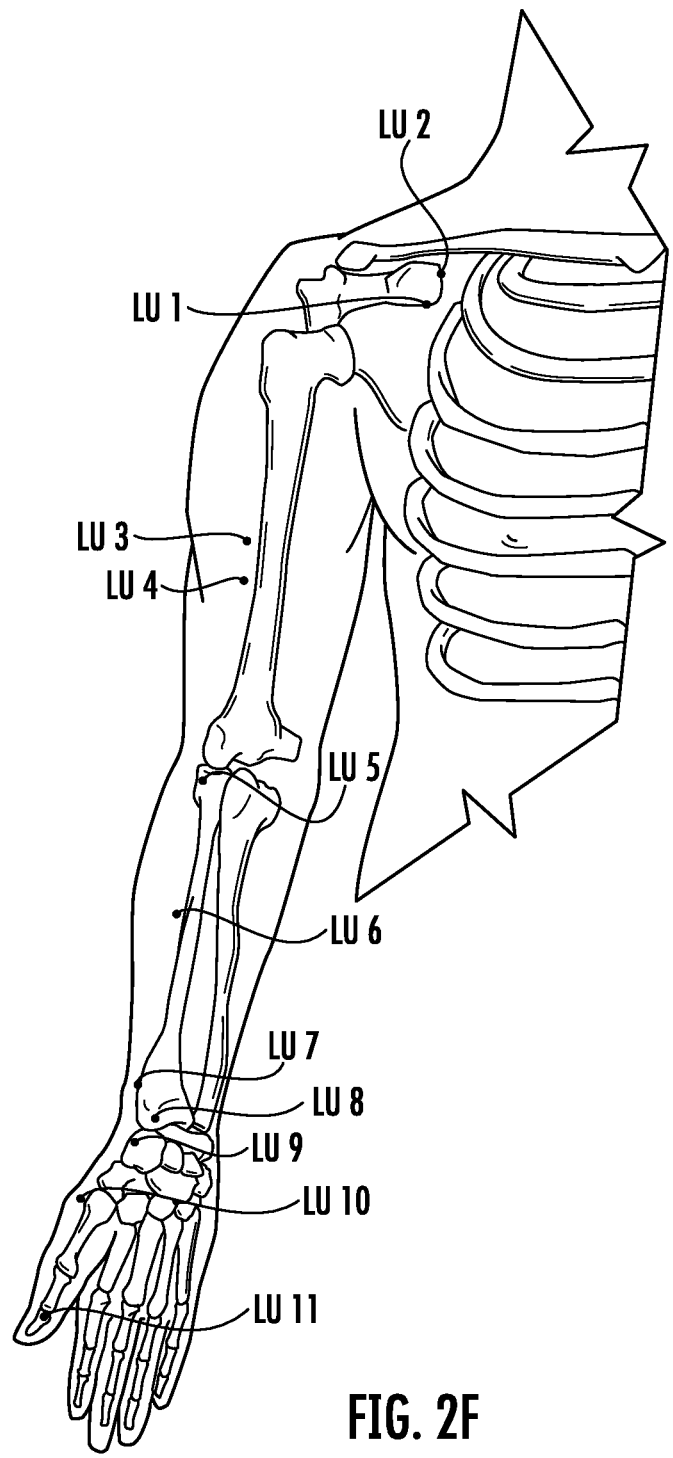
Figure 2G:
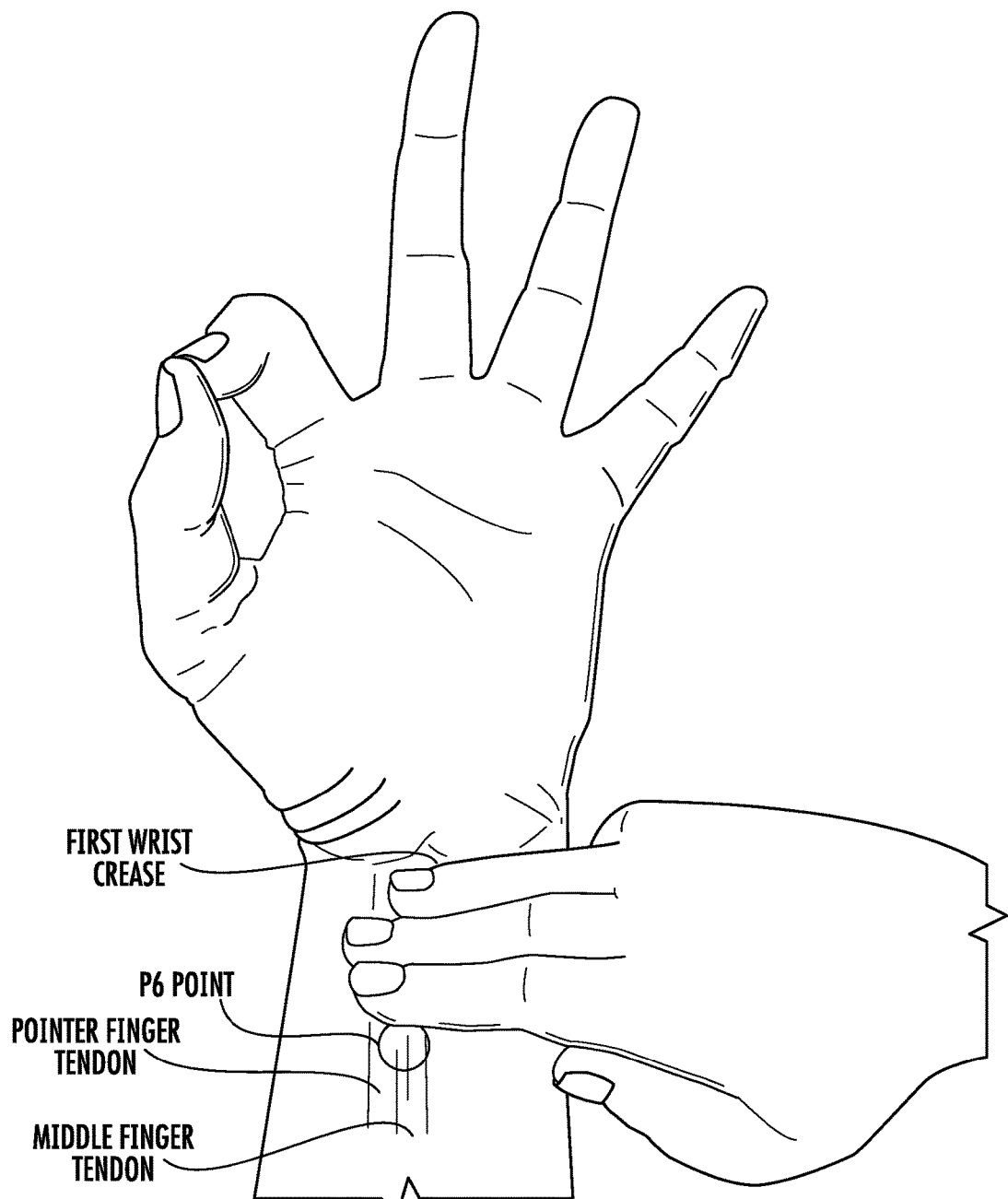
Figure 2H:
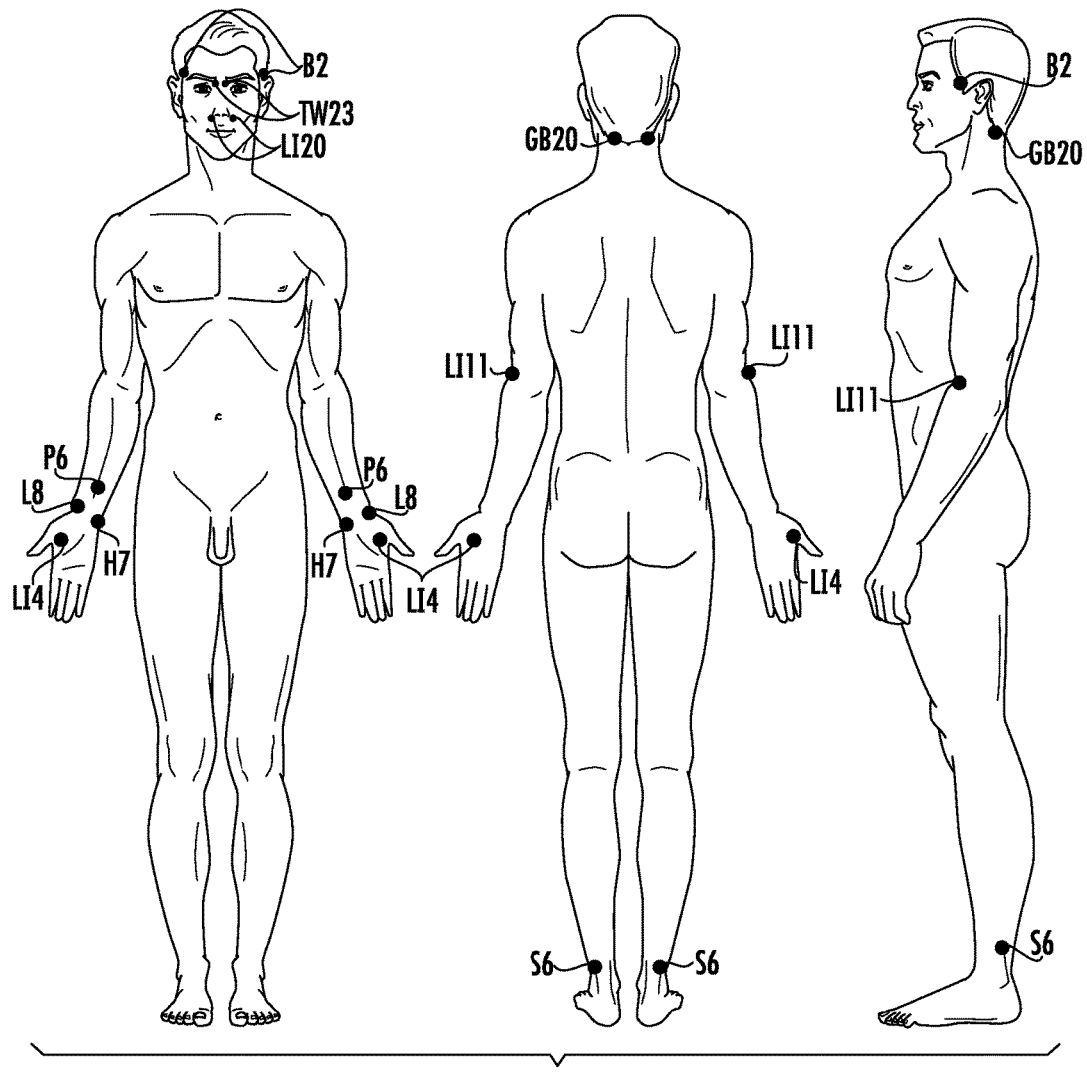

The acupressure device 14 may be configured in any manner to apply pressure to one or more pressure points on a mammal. For example, the acupressure device 14 may include one or more raised elements that may apply pressure to the one or more pressure points on the mammal. The raised elements may be formed as a part of the material of the acupressure device 14, may be one or more inserts that may be temporarily attached to the acupressure device 14, or may be fixedly (and/or permanently) attached to the acupressure device 14. Furthermore, the raised elements may have any shape and/or size for applying pressure. Examples of a raised element are discussed below in additional detail with regard to FIGS. 3a-3e. The acupressure device 14 may be configured apply pressure to any number of pressure points on the mammal. For example, the acupressure device 14 may be configured to apply pressure to one pressure point, two pressure points, three pressure points, four pressure points, five pressure points, ten pressure points, or any other number of pressure points on the mammal. The acupressure device 14 may be configured to apply pressure to any pressure point on a mammal (or any one or more pressure points on the mammal). For example, the acupressure device 14 may be configured to apply pressure to one or more of ST1-ST30 (examples of which are illustrated in FIG. 2a), PC1-PC9 (examples of which are illustrated in FIG. 2b), TH1-TH23 (examples of which are illustrated in FIG. 2c), GB1-GB44 (examples of which are illustrated in FIGS. 2d and 2e), LU1-LU11 (examples of which are illustrated in FIG. 2f), P6 (an example of which is illustrated in FIG. 2g), LI4 (an example of which is illustrated in FIG. 2h), L8 (an example of which is illustrated in FIG. 2h), H7 (an example of which is illustrated in FIG. 2h), LI20 (an example of which is illustrated in FIG. 2h), B2 (an example of which is illustrated in FIG. 2h), GB20 (an example of which is illustrated in FIG. 2h), TW23 (an example of which is illustrated in FIG. 2h), S6 (an example of which is illustrated in FIG. 2h), any of the pressure points listed in Table 1 (below), any other pressure points on any mammal, or any other documented acupressure points known for therapeutic value. In particular embodiments, the acupressure device 14 may be configured to apply pressure to one or more pressure points on a mammal by applying pressure directly or indirectly to the skin (or fur or hair) of the mammal. For example, the acupressure device 14 may be in direct contact with the skin of a person, and may apply pressure directly to the skin in order to apply pressure to one or more pressure points of the person. As another example, the acupressure device 14 may be in indirect contact with the skin of a person (e.g., the person may be wearing a garment, such as a shirt, suit, or wetsuit, that prevents the acupressure device 14 from being in direct contact with the skin of the person), and may apply pressure indirectly to the skin (e.g., through the garment) in order to apply pressure to one or more pressure points of the person. In particular embodiments, the acupressure device 14 may also be configured to apply pressure at a location substantially positioned at any of the above-listed pressure points (or other points). A location substantially positioned at any of the above-listed pressure points (or other points) may refer to a location positioned at or within 2 inches of the pressure point (or other point). In particular embodiments, the acupressure device 14 may apply pressure at a location substantially positioned at any of the above-listed pressure points (such as P6, for example) due to, for example, user error with the acupressure device. For example, a user (such as a person) may improperly place the acupressure device 14 near the P6 pressure point, but not at the P6 pressure point.

The acupressure device 14 may be configured to provide any therapeutic relief and/or health benefit. For example, the acupressure device 14 may be configured to provide nausea relief (such as relief from pregnancy induced nausea, morning sickness induced nausea, c-section induced nausea, post-operative nausea, exercise induced nausea, air sickness induced nausea, water sickness induced nausea, car sickness induced nausea, travel sickness induced nausea, headache induced nausea, vertigo induced nausea, chemotherapy induced nausea, hangover related nausea, or any other nausea or nausea-like symptoms), stress relief and/or relaxation, dizziness relief, cough, cold, and/or flu relief, sleep and/or insomnia relief, pain and/or burning relief, headache and/or migraine relief, nasal congestion and/or allergy relief, constipation relief, induction into labor for pregnancy, tendinitis relief, tension relief, spasm relief, fatigue relief, leg and/or foot cramp relief, calm gastrointestinal dysfunction, open nasal passages, promote bronchodilation, mask unpleasant smells, provide a calming effect on emotions, relieve acute and/or chronic neck pain, relieve anxiety, relieve stress, relieve carpal pain, provide any other acupressure effect, or any combination of the preceding.

The acupressure device 14 may be configured to apply pressure to one or more specific pressure points on a mammal in order to provide one or more specific types of therapeutic relief and/or health benefits. For example, in order to provide nausea relief, the acupressure device 14 may be configured to apply pressure to one or more of the following pressure points: P6, LI4, PC3, CV11, CV2, CV22, and ST36. As another example, in order to provide stress relief and/or relaxation, the acupressure device 14 may be configured to apply pressure to one or more of the following pressure points: LV3, H7, K27, K3, SP9, LI4, ST36, TW5, LI11, CV17, GV24, GB13, P6, B60, and GV16. As a further example, in order to provide dizziness relief, the acupressure device 14 may be configured to apply pressure to one or more of the following pressure points: P6, LI2, GB35, ST36, GV26, P6, TW5, and K3. As another example, in order to provide cough, cold, and/or flu relief, the acupressure device 14 may be configured to apply pressure to one or more of the following pressure points: L8, B36, B2, LI20, ST3, LI11, L14, GB20, GV16, GV24.5, LI2, L8, B10, EX17, K27, B36, CV22, LI3, LI7, LI18, LI19, LI20, LI14, SP9, ST36, K3, B60, and TW5. As another example, in order to provide sleep and/or insomnia relief, the acupressure device 14 may be configured to apply pressure to one or more of the following pressure points: H7, B6, B62, K6, GB20, GV16, and P6. As a further example, in order to provide pain and/or burning relief, the acupressure device 14 may be configured to apply pressure to one or more of the following pressure points: LI2, LI3, LI4, LI5, LI7, LI8, LI10, LI11, LI12, LI13, LI14, LI15, LI16, LI17, LI18, GB20, and GV16. As another example, in order to provide headache and/or migraine relief, the acupressure device 14 may be configured to apply pressure to one or more of the following pressure points: LI4, GB41, LV3, GB38, ST44, P6, LI5, LI7, B2, GB20, GV16, TW23, and K27. As a further example, in order to provide nasal congestion relief and/or allergy relief, the acupressure device 14 may be configured to apply pressure to one or more of the following pressure points: LI5, LI19, B3, LI4, F1, F2, F3, LI20, B36, GB20, and GV24.5. As another example, in order to provide constipation relief, the acupressure device 14 may be configured to apply pressure to one or more of the following pressure points: LI11, CV6, CV8, CV12, CV16, and CV13. As a further example, in order to provide induction into labor for pregnancy, the acupressure device 14 may be configured to apply pressure to one or more of the following pressure points: LI4, BI31, BI32, GV1, CO4, SP9, SP6, GB21, LI3, CV4, and ST36. As another example, in order to provide tendinitis relief, the acupressure device 14 may be configured to apply pressure to one or more of the following pressure points: P6, P3, P7, and HT7. As a further example, in order to provide tension relief, the acupressure device 14 may be configured to apply pressure to one or more of the following pressure points: GV16, BB20, TW16, B10, GB21, K1, HT7, and P6. As another example, in order to provide spasm relief, the acupressure device 14 may be configured to apply pressure to one or more of the following pressure points: K27, LI1, St13, St1, St3, CV22, GV26, St16, St2, B1, LI4, GB20, GV16, GV24.5, St36, K3, B60, GB21, CV6, GB34, B57, LV3, LI11, B10, TW16, B2, TW15, LI14, B40, B23, B50, GB40, and GB41. As a further example, in order to provide fatigue relief, the acupressure device 14 may be configured to apply pressure to one or more of the following pressure points: LU1, CV6, LU2, CV4, and CV3. As another example, in order to provide leg and/or foot cramp relief, the acupressure device 14 may be configured to apply pressure to one or more of the following pressure points: LV3, GB41, SP6, ST36, K1, SP12, B40, and B52.

The acupressure device 14 may be formed (or otherwise be made) from any material. For example, the acupressure device 14 may be rubber, latex, latex-free rubber, plastic, a polymer, a ceramic, glass, metal, an aroma-permeable material, any other material, or any combination of the preceding. In particular embodiments, the acupressure device 14 may be any material capable of absorbing, binding, or retaining (in some manner) an amount of therapeutic substance 18. In particular embodiments, the acupressure device 14 may be formed from two or more of the above-listed materials. In particular embodiments, the acupressure device may be a thermoplastic vulcanite injected moldable latex-free rubber band. The acupressure device 14 may have any size (e.g., length, width, thickness, etc.), and the size may vary based on the mammal for which the acupressure device 14 is designed. For example, the size of the acupressure device 14 may be larger for an adult human than for a child human. As another example, the size of the acupressure device 14 may be larger for a horse than for a dog.

The acupressure device 14 may have an adjustable size. For example, the acupressure device 14 may have a length that may be adjusted by the human. In such an example, the human may adjust the length to be smaller, or to be bigger. The size of the acupressure device 14 may be adjusted in any manner. For example, the acupressure device 14 may have a first end that is separated from a second end. In such an example, the first end may have two or more holes that extend along the first end at different locations, and the second end may have a buckle or peg configured to fit into one of the holes. As such, the user may adjust the length of the acupressure device 14 by selecting a particular hole to fit the buckle or peg into. As other examples, the size of the acupressure device 14 may be adjusted using a watch-like buckle or snap, velcro, a sliding mechanism, or any other adjustment mechanism. In particular embodiments, adjusting the size of the acupressure device 14 may increase or decrease the amount of pressure applied to one or more pressure points by the acupressure device 14. The acupressure device 14 may alternatively have a non-adjustable size. For example, the acupressure device 14 may be a single size band that is formed as a continuous loop. In such an example, the single size band may have a bigger single size for bigger mammals and/or a smaller single size for smaller mammals. In particular embodiments, the single size acupressure device 14 may be flexible so as to expand (at least partially) to fit various sized mammals.

The acupressure device 14 may be configured to be wearable by a mammal. For example, the acupressure device 14 may be worn on the mammal's head, arm, leg, wrist, appendage, skin, fur, hair, any other location on the mammal's body that may allow the acupressure device 14 to provide pressure to one or more pressure points, or any combination of the preceding. The acupressure device 14 may be configured to be worn at any location and/or while the mammal is performing any activity. For example, the acupressure device 14 may be sized and/or shaped to be worn in the car, in an airplane, at the beach, in the water, in the hospital, any other location, or any combination of the preceding. Furthermore, the acupressure device 14 may be lightweight and/or portable, allowing the acupressure device 14 to be easily transported between locations (even while be worn by the mammal). As another example, the acupressure device 14 may be sized and/or shaped to be worn while working, exercising, running, swimming, receiving medical treatment, attending school classes, performing any other activity, or any combination of the preceding. In particular embodiments, the acupressure device 14 may be waterproof, so as to allow the acupressure device 14 to be worn in the water.

As is further illustrated, the therapeutic substance and acupressure system 10 further includes a therapeutic substance 18 coupled to the acupressure device 14. The therapeutic substance 18 may be configured to provide one or more beneficial effects on the body and/or mind of the mammal. For example, the therapeutic substance 18 may be configured to provide nausea relief, stress relief and/or relaxation, dizziness relief, cough, cold, and/or flu relief, sleep and/or insomnia relief, pain and/or burning relief, headache and/or migraine relief, nasal congestion and/or allergy relief, constipation relief, induction into labor for pregnancy, tendinitis relief, tension relief, spasm relief, fatigue relief, leg and/or foot cramp relief, calm gastrointestinal dysfunction, open nasal passages, promote bronchodilation, mask unpleasant smells, provide a calming effect on emotions, relieve acute and/or chronic neck pain, relieve anxiety, relieve stress, relieve carpal pain, operate as an antiseptic, provide skin revitalization, provide general tonic qualities, provide a soothing effect on a mammal, provide any other aromatherapy effect, or any combination of the preceding.

The therapeutic substance 18 may be any substance configured to provide one or more beneficial effects on the body and/or mind of the mammal. For example, the therapeutic substance 18 may be an aromatic substance that provides one or more beneficial effects on the body and/or mind. Examples of such an aromatic substance may include oils, essential oils, aromatic compounds, any scented substance (such as a peppermint scented substance, or a substance having any of the scents listed below), any other aromatic substance, or any combination of the preceding. As another example, the therapeutic substance 18 may be a substance for transdermal application. Examples of such a substance for transdermal application may include chemical compounds, essential oils, medicines, oils, any other transdermal substance, or any combination of the preceding. The therapeutic substance 18 may be delivered to the mammal in any suitable manner. As an example, the aroma (or scent) of the therapeutic substance 18 may be received by the mammal through inhalation. As a further example, the aroma of the therapeutic substance 18 may be received by the mammal's olfactory receptors. As another example, the therapeutic substance 18 may be transdermally received by the mammal (e.g., received through the skin of the mammal). The essential oils when contacting the skin will permeate thru the pores of the epidermis and reach the blood stream for therapeutic value.

As is discussed above, the therapeutic substance 18 may be an essential oil. An essential oil may refer to a concentrated hydrophilic liquid containing volatile compound derived from plants. The essential oil may contain the characteristic fragrance (or aroma or scent) of the plant from which it is derived. The essential oil may be derived (or have the scent of) any portion of a plant, such as a whole flower, a petal, bark, leaves, twigs, a whole fruit, fruit rind, seeds, roots, sap, resins, any other portion of the plant, or any combination of the preceding. Therapeutic substance 18 may include an essential oil derived from (or having the scent of) one or more of the following plants: agar, ajwain, aloe vera, almond kernel, angelica, anise, apricot kernel, asafoetida, avocado, balsam of Peru, basil, bay, benzoin, bergamot, birch, black pepper, boil de rose, borage, buchu, cajeput, calamus, camphor, *cannabis sativa*, caraway, cardamom, carrot, cedar, chamomile, camomile mataricaria, chamomile roman, cinnamon, citronella, clary-sage, clove, coriander, corn, costmary, cranberry, cubeb, cumin, cypress, cypriol, curry, davana, dill, elecampane, *eucalyptus, eucalyptus* lemon, *eucalyptus* peppermint, *eucalyptus radiata*, evening primrose, fennel, fenugreek, frankincense, galangal, galbanum, geranium, ginger, goldenrod, grapefruit, grapeseed, hazelnut, hemp, henna, helichrysum, hickory, horseradish, hops, hyssop, Idaho tansy, immortelle, inula odorata, jasmine, jojoba, juniper, *Laurus nobilis*, lavender, ledum, lemon, lemon grass, lime, *litsea cubeba*, linaloe, mace, mandarin orange, marjoram, melaleuca, melissa, menthe arvensis, mountain savory, mugwort, mustard, myrrh, myrtle, neem, neroli, niaouli, nutmeg, olive, orange, oregano, orris, palma rose, palo santo, parsley, patchouli, peach kernel, peanut, pennyroyal, peppermint (such as Indian peppermint), perilla, petitgrain, pimento, pine, ravensara, red cedar, red thyme, roman chamomile, rose, rosehip, rose bulger, rose maroc, rosemary, rosewood, sage, sandalwood, sassafras, savory, schisandra, sesame, soya, spearmint, spikenard, spruce, star anise, sunflower, sweet almond, tagetes, tangerine, tarragon, tea tree, thyme, thyme red, tsuga, turmeric, valerian, vetiver, violet, western red cedar, wheat germ, wintergreen, yarrow, ylang-ylang, zedoary, any other plant listed below in Table 1, or any other plant that may provide one or more beneficial effects on the body and/or mind of the mammal.

The therapeutic substance 18 coupled to the acupressure device 14 may be selected to provide one or more specific health benefits. For example, in order to provide nausea relief, the therapeutic substance 18 may be derived from (or have the scent of) one or more of the following plants: peppermint, *cannabis*, hemp, ginger, di-gize, fennel, patchouli, nutmeg, wintergreen, spearmint, and tarragon. As another example, in order to provide pain relief, the therapeutic substance 18 may be derived from (or have the scent of) one or more of the following plants: marjoram, peppermint, balsam fir, basil, birch, cypress, ginger, lavender, lemongrass, rosemary, silver fir, spanish sage, vetiver, white fir, wintergreen, copaiba, roman chamomile, *eucalyptus*, oregano, clove, thyme, and helichrysum. As a further example, in order to act as a vasodilating agent, the therapeutic substance 18 may be derived from (or have the scent of) one or more of the following plants: lemon grass, carrot seed, canadian fleabane, lavender, wintergreen, and birch bark. As another example, in order to promote sleep, the therapeutic substance 18 may be derived from (or have the scent of) one or more of the following plants: lavender, frankincense, ylang ylang, vetiver, roman chamomile, bergamot, sandalwood, marjoram, and valerian. As a further example, in order to relieve stress and/or promote relaxation, the therapeutic substance 18 may be derived from (or have the scent of) one or more of the following plants: cedar wood, lemon, frankincense, lavender, bergamot, chamomile german, chamomile roman, geranium, jasmine, marjoram, orange blossom, rose, sandalwood, valerian, and ylang ylang. As another example, in order to provide cough, cold, and/or flu relief, the therapeutic substance 18 may be derived from (or have the scent of) one or more of the following plants: thieves, myrtle, pine, *eucalyptus*, Idaho balsam fir, raven, tea tree, ravansara, and clove. As a further example, in order to provide dizziness relief, the therapeutic substance 18 may be derived from (or have the scent of) one or more of the following plants: peppermint, frankincense, cedar wood, ginger, and patchouli. As another example, in order to provide pain relief, the therapeutic substance 18 may be derived from (or have the scent of) one or more of the following plants: wintergreen, *eucalyptus*, lavender, frankincense, and lemon. As a further example, in order to provide headache and/or migraine relief, the therapeutic substance 18 may be derived from (or have the scent of) one or more of the following plants: peppermint, lavender, rosemary, *eucalyptus*, helichrysum, spearmint, and roman chamomile. As another example, in order to provide constipation relief, the therapeutic substance 18 may be derived from (or have the scent of) one or more of the following plants: peppermint, di-gize, ginger, orange, rosemary, basil, lemon, fennel, rose, black pepper, and majoram. As a further example, in order to provide nasal congestion relief and/or allergies relief, the therapeutic substance 18 may be derived from (or have the scent of) one or more of the following plants: wintergreen, lavender, chamomile, lemon, *eucalyptus*, peppermint, benzoin, clove, marjoram, tea tree, and thyme. As another example, in order to induce labor in pregnancy, the therapeutic substance 18 may be derived from (or have the scent of) one or more of the following plants: clary sage, geranium, jasmine, lavender, peppermint, rose, ylang ylang, myrrh, frankincense, and helichrysum. As a further example, in order to suppress appetite, the therapeutic substance 18 may be derived from (or have the scent of) one or more of the following plants: nutmeg, ginger, orange, spearmint, bergamot, sandalwood, grapefruit, and ocotea. As another example, in order to provide menstrual cramp relief, the therapeutic substance 18 may be derived from (or have the scent of) one or more of the following plants: dragon time, lavender, clary sage, peppermint, *eucalyptus*, rose, geranium, ylang ylang, and salvia. As another example, in order to reduce tendinitis, the therapeutic substance 18 may be derived from (or have the scent of) one or more of the following plants: lavender and marjoram. As a further example, in order to reduce tension, the therapeutic substance 18 may be derived from (or have the scent of) one or more of the following plants: marjoram, helichrysum, lavender, peppermint, and roman chamomiles. As another example, in order to reduce spasms, the therapeutic substance 18 may be derived from (or have the scent of) one or more of the following plants: basil, marjoram, roman chamomile, clary sage, cypress, lavender, and peppermint. As a further example, in order to reduce fatigue, the therapeutic substance 18 may be derived from (or have the scent of) one or more of the following plants: cypress, marjoram, peppermint, white fir, *eucalyptus*, grapefruit, rosemary, and thyme. As another example, in order to reduce leg and/or foot cramps, the therapeutic substance 18 may be derived from (or have the scent of) one or more of the following plants: marjoram, lemongrass, peppermint, basil, clary sage, cypress, grapefruit, lavender, rosemary, and vetiver.

The therapeutic substance 18 coupled to the acupressure device 14 may be selected to provide specific health benefits consistent (or identical) with the specific health benefits provided by the acupressure device 14. For example, if the acupressure device 14 is configured to apply pressure to one or more pressure points to provide, for example, nausea relief, the therapeutic substance 18 coupled to the acupressure device 14 may be selected to also provide, for example, nausea relief. Examples of pressure points and therapeutic substances 18 that may provide consistent (or identical) specific health benefits are listed below in Table 1. The acupressure device 14 may be configured to apply pressure to any one or more of the below listed pressure points for a specific health benefit (such as nausea relief, for example), and the therapeutic substance 18 coupled to acupressure device may be selected from any one or more of the below-listed therapeutic substances for the consistent (or identical) specific health benefit (such as nausea relief, for example):

| Health Benefit | Pressure Point(s) | Therapeutic substance(s) 18 |
|---|---|---|
| Nausea Relief | P6 | Peppermint |
| | LI4 | Cannabis |
| | PC3 | Hemp |
| | CV11 | Ginger |
| | CV2 | di-gize |
| | CV22 | fennel |
| | ST36 | *patchouli* |
| | | nutmeg |
| | | wintergreen |
| | | spearmint |
| | | *tarragon* |
| Stress Relief and/or Relaxation | LV3 | Cedar wood |
| | H7 | Lemon |
| | K27 | Frankincense |
| | K3 | Lavender |
| | SP9 | Bergamot |
| | LI4 | Chamomile german |
| | ST36 | Chamomile roman |
| | TW5 | *Geranium* |
| | LI11 | Jasmine |
| | CV17 | Marjoram |
| | GV24 | Orange blossom |
| | GB13 | Rose |
| | P6 | Sandalwood |
| | B60 | Valerian |
| | GV16 | Ylang ylang |
| Dizziness Relief | P6 | Peppermint |
| | LI2 | Frankincense |
| | GB35 | Cedar wood |
| | ST36 | Ginger |
| | GV26 | *patchouli* |
| | P6 | |
| | TW5 | |
| | K3 | |
| Cough, Cold, and/or Flu Relief | L8 | Thieves |
| | B36 | Myrtle |
| | B2 | Pine |
| | LI20 | *Eucalyptus* |
| | ST3 | Idaho balsam fir |
| | LI11 | Raven |
| | LI4 | Tea tree |
| | GB20 | *Ravansara* |
| | GV16 | Clove |
| | GV24.5 | |
| | LI2 | |
| | L8 | |
| | B10 | |
| | EX17 | |
| | K27 | |
| | B36 | |
| | CV22 | |
| | LI3 | |
| | LI7 | |
| | LI18 | |
| | LI19 | |
| | LI20 | |

-continued

| Health Benefit | Pressure Point(s) | Therapeutic substance(s) 18 |
| --- | --- | --- |
| | LI14 | |
| | SP9 | |
| | ST36 | |
| | K3 | |
| | B60 | |
| | TW5 | |
| Sleep and/or Insomnia Relief | H7 | Lavender |
| | B6 | Frankincense |
| | B62 | Ylang ylang |
| | K6 | Vetiver |
| | GB20 | Roman chamomile |
| | GV16 | Bergamot |
| | P6 | Sandalwood |
| | | Marjoram |
| | | valerian |
| Pain and/or Burning Relief | LI2 | Marjoram |
| | LI3 | Peppermint |
| | LI4 | Balsam fir |
| | LI5 | Basil |
| | LI7 | Birch |
| | LI8 | Cypress |
| | LI10 | Ginger |
| | LI11 | Lavender |
| | LI12 | Lemongrass |
| | LI13 | Rosemary |
| | LI14 | Silver fir |
| | LI15 | Spanish sage |
| | LI16 | Vetiver |
| | LI17 | White fir |
| | LI18 | Wintergreen |
| | GB20 | Copaiba |
| | GV16 | Roman chamomile |
| | | *Eucalyptus* |
| | | Oregano |
| | | Clove |
| | | Thyme |
| | | *Helichrysum* |
| | | lemon |
| Headache and/or Migraine Relief | LI4 | peppermint |
| | GB41 | lavender |
| | LV3 | rosemary |
| | GB38 | *eucalyptus* |
| | ST44 | *helichrysum* |
| | P6 | spearmint |
| | LI5 | roman chamomile |
| | LI7 | |
| | B2 | |
| | GB20 | |
| | GV16 | |
| | K27 | |
| | TW23 | |
| Nasal Congestion and/or Allergy Relief | LI5 | Wintergreen |
| | LI19 | Lavender |
| | B3 | Chamomile |
| | LI4 | Lemon |
| | F1 | *Eucalyptus* |
| | F2 | Benzoin |
| | F3 | Clove |
| | LI20 | Marjoram |
| | B36 | Tea tree |
| | GB20 | Thyme |
| | GV24.5 | |
| Constipation Relief | LI11 | Peppermint |
| | CV6 | di-gize |
| | CV8 | ginger |
| | CV12 | orange |
| | CV16 | rosemary |
| | CV13 | basil |
| | | lemon |
| | | fennel |
| | | rose |
| | | black pepper |
| | | majoram |
| Induction into Labor for pregnancy | LI4 | Clary sage |
| | BI31 | *Geranium* |
| | BI32 | Jasmine |
| | GV1 | Lavender |

-continued

| Health Benefit | Pressure Point(s) | Therapeutic substance(s) 18 |
| --- | --- | --- |
| | CO4 | Peppermint |
| | SP9 | Rose |
| | SP6 | Ylang ylang |
| | GB21 | Myrrh |
| | LI3 | Frankincense |
| | CV4 | *helichrysum* |
| | ST36 | |
| Tendinitis Relief | P6 | lavender |
| | P3 | marjoram |
| | P7 | |
| | HT7 | |
| Tension Relief | GV16 | Marjoram |
| | BB20 | *Helichrysum* |
| | TW16 | Lavender |
| | B10 | Peppermint |
| | GB21 | Roman chamomile |
| | K1 | |
| | HT7 | |
| | P6 | |
| Spasm Relief | K27 | Basil |
| | LI1 | Marjoram |
| | St13 | Roman chamomile |
| | St1 | Clary |
| | St3 | Sage |
| | CV22 | Cypress |
| | GV26 | Lavender |
| | ST16 | peppermint |
| | ST2 | |
| | B1 | |
| | LI4 | |
| | GB20 | |
| | GV16 | |
| | GV24.5 | |
| | ST36 | |
| | K3 | |
| | B60 | |
| | GB21 | |
| | CV6 | |
| | GB34 | |
| | B57 | |
| | LV3 | |
| | LI11 | |
| | B10 | |
| | TW16 | |
| | B2 | |
| | TW15 | |
| | LI14 | |
| | B40 | |
| | B23 | |
| | B50 | |
| | GB40 | |
| | GB41 | |
| Fatigue Relief | LU1 | Cypress |
| | CV6 | Marjoram |
| | LU2 | Peppermint |
| | CV4 | White fir |
| | CV3 | *Eucalyptus* |
| | | Grapefruit |
| | | Rosemary |
| | | thyme |
| Leg and/or Foot cramp relief | LV3 | Marjoram |
| | GB41 | Lemongrass |
| | SP6 | Peppermint |
| | SP36 | Basil |
| | K1 | Clary sage |
| | SP12 | Cypress |
| | B40 | Grapefruit |
| | B52 | Lavender |
| | | Rosemary |
| | | vitiver |

In particular embodiments, when both the acupressure device and the therapeutic substance 18 provide consistent (or identical) benefits, the therapeutic substance 18 may provide a more rapid benefit to the mammal while the acupressure device 14 may provide a more delayed, but potentially longer, benefit.

The therapeutic substance 18 may be coupled to the acupressure device 14 in any manner. For example, the therapeutic substance 18 may be infused into the acupressure device 14, incorporated into the acupressure device 14 during the manufacturing process, topically applied to the acupressure device 14, provided as a coating on the acupressure device 14, sprayed onto the acupressure device 14, positioned within a container in the acupressure device 14, coupled to the acupressure device 14 in any other manner, or any combination of the preceding. Coupling the therapeutic substance 18 to the acupressure device 14 may refer to coupling the therapeutic substance 18 to all or a portion of the acupressure device 14. As is discussed above, the therapeutic substance 18 may be infused into the acupressure device 14. The therapeutic substance 18 may be infused into the acupressure device 14 in any manner. As one example, the therapeutic substance 18 in liquid form may be mixed together with the material of the acupressure device 14 (such as thermoplastic vulcanite (TPV)) in liquid form, the mixture may be poured into a mold of the acupressure device 14, and the mixture may be cooled to form the therapeutic substance and acupressure system 10. As is also discussed above, the acupressure device 14 may include a container that includes the therapeutic substance 18. The container may be any type of container, such as a capsule, a blister, a pocket, a vessel, or any other type of container. The container may be a time-release container, allowing the therapeutic substance 18 to be released gradually. The container may be configured to open, allowing the mammal (such as human) to break (or otherwise open the seal of the container) in order to release the therapeutic substance 18 (such as all or a portion of the therapeutic substance 18).

Any amount of the therapeutic substance 18 may be coupled to the acupressure device 14. For example, the therapeutic substance 18 may make up 0.01% of the weight basis of the acupressure device 14 (where the weight basis may refer to the entire weight of the acupressure device 14 with the therapeutic substance 18), 0.05% of the weight basis of the acupressure device 14, 0.1% of the weight basis of the acupressure device 14, 0.5% of the weight basis of the acupressure device 14, 1% of the weight basis of the acupressure device 14, 3% of the weight basis of the acupressure device 14, 5% of the weight basis of the acupressure device 14, 10% of the weight basis of the acupressure device 14, 15% of the weight basis of the acupressure device 14, 20% of the weight basis of the acupressure device 14, 25% of the weight basis of the acupressure device 14, 30% of the weight basis of the acupressure device 14, 40% of the weight basis of the acupressure device 14, or any other amount of the weight basis of the acupressure device 14. As another example, the therapeutic substance 18 may make up the following ranges of the weight basis of the acupressure device 14: 0.01%-40% of the weight basis of the acupressure device 14, 0.01%-30% of the weight basis of the acupressure device 14, 0.01%-20% of the weight basis of the acupressure device 14, 0.01%-15% of the weight basis of the acupressure device 14, 0.01%-10% of the weight basis of the acupressure device 14, 0.01%-5% of the weight basis of the acupressure device 14, 0.5%-20% of the weight basis of the acupressure device 14, 1.0%-20% of the weight basis of the acupressure device 14, 5%-20% of the weight basis of the acupressure device 14, or any other range of the weight basis of the acupressure device 14. As a further example, the therapeutic substance 18 may be an amount that is dried up (or empty, or evaporated, or the scent is otherwise no longer emitted from the acupressure device 14) when exposed to air for 6 hours, 12 hours, 18 hours, 24 hours, 48 hours, 72 hours, 96 hours, 120 hours, 144 hours, or any amount of time less than 144 hours. In particular embodiments, when the therapeutic substance 18 is dried up (or empty, or evaporated, or the scent is otherwise no longer emitted from the acupressure device 14), another amount of therapeutic substance 18 may be re-coupled to the acupressure device 14 (such as re-applied by the user). In particular embodiments, when the therapeutic substance 18 is dried up (or empty, or evaporated, or the scent is otherwise no longer emitted from the acupressure device 14), the acupressure device 14 may be disposed of and replaced with a new acupressure device 14 having a new amount of therapeutic substance 18 coupled to it.

Modifications, additions, or omissions may be made to system 10 without departing from the scope of the invention. For example, any number of therapeutic substances 18 (such as one, two, three, four, or five or more) may be coupled to acupressure device 14. As another example, any number of acupressure devices 14 (such as one, two, three, four, or five or more) may be utilized by a mammal at the same time, and to provide any number of health benefits. As a further example, the acupressure device(s) 14 and the therapeutic substance(s) 18 used by a mammal at the same time may provide any number of benefits to the mammal, such as one, two, three, four, or five or more benefits. In such an example, the mammal may utilize a single acupressure device 14 (or more than one acupressure device 14) with one or more therapeutic substances 18 to provide multiple benefits simultaneously, such as nausea relief and stress relief, for example. As another example, one or more additional substances may be coupled or added to acupressure device 14 and/or the therapeutic substance 18 to provide additional benefits. In such an example, one or more of the following additional substances may be coupled or added to acupressure device 14 and/or the therapeutic substance 18: an anti-irritant, a cleansing agent, an antiseptic, a colorant, a pigment, a filler, an antioxidant, a moisturizer, a skin reconditioning agent, a vitamin, a nutritional supplement, an anesthetic agent, a cosmetic agent, any other therapeutic agent, or any combination of the preceding.

Figure 3A:
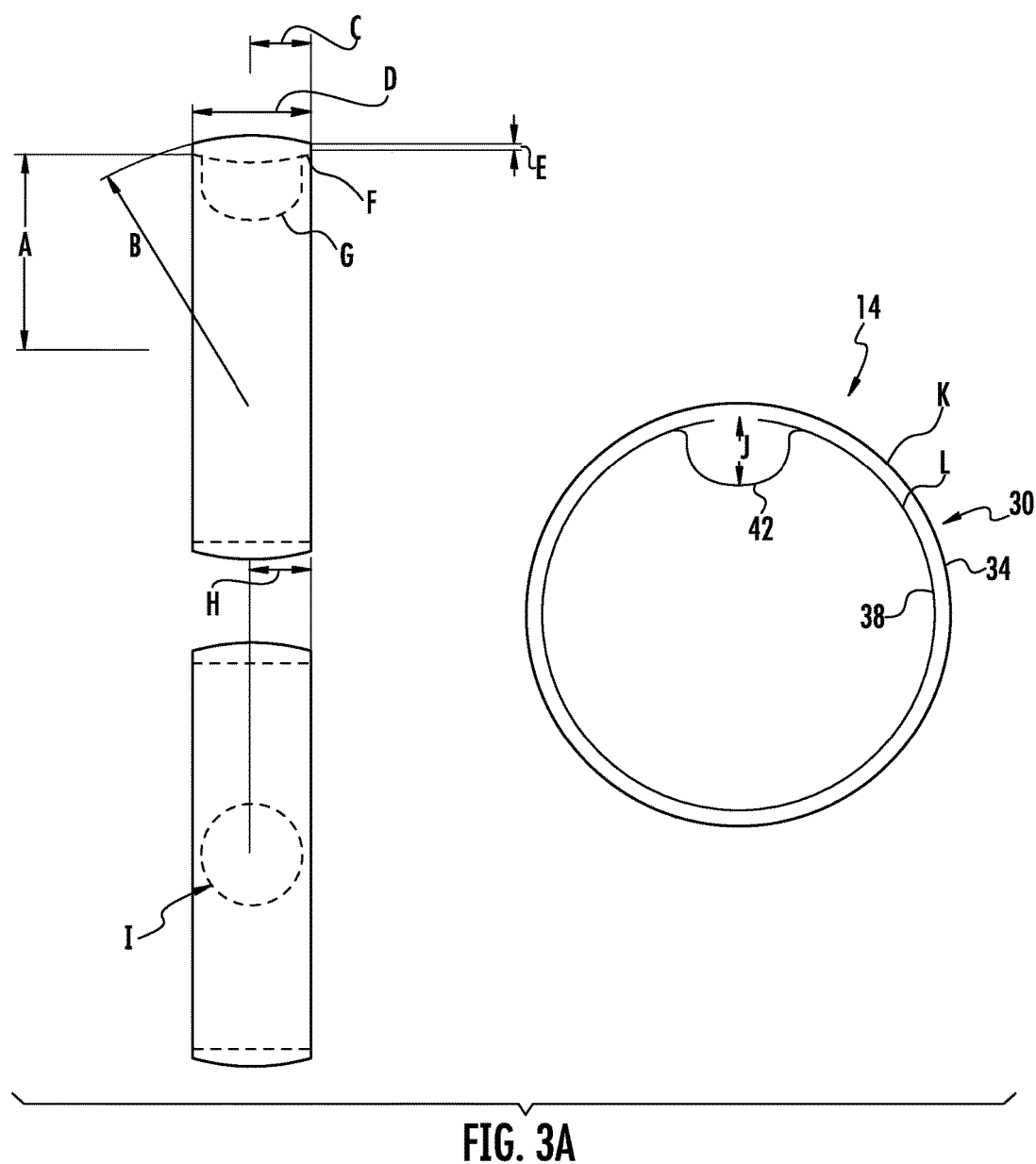
Figure 3B:
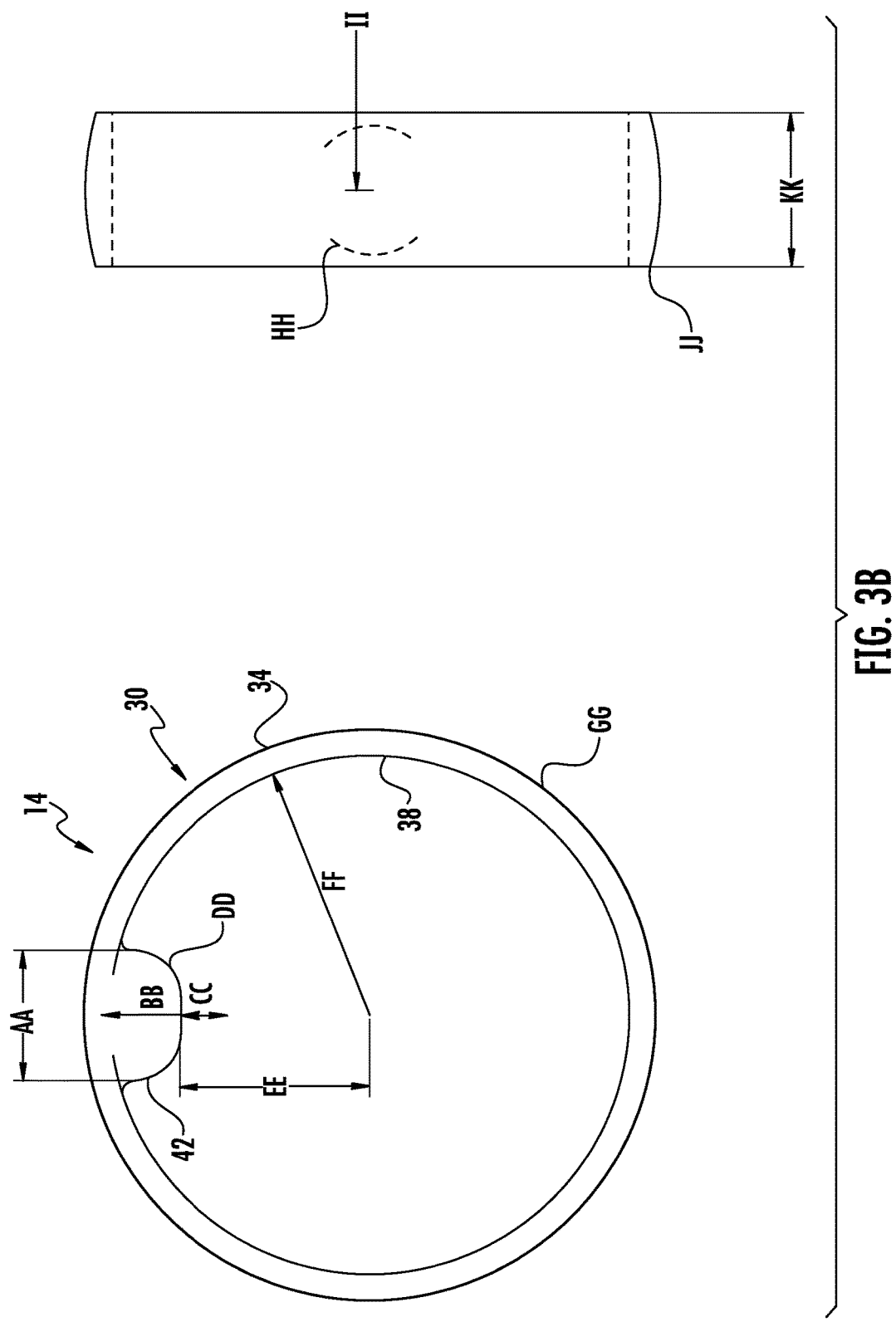

FIGS. 3a-3b illustrate examples of an acupressure device of FIG. 1. As illustrated, the acupressure device 14 may be a wrist band (or appendage band) that may be worn by a mammal (such as an adult human, a child human, a dog, a cat, a horse, or any other mammal) on the mammal's wrist (or other appendage, such as a leg of a dog).

According to the illustrated embodiment, the acupressure device 14 includes a band 30. The band 30 is configured to encircle a wrist of the mammal (such as an adult human) or an appendage of the mammal (such as a leg of a dog). As illustrated, the band 30 is a continuous loop. In such an embodiment, the band 30 may be a single size band that may be flexible so as to expand (at least partially) to fit various sized mammals. In particular embodiments, the band 30 may be an adjustable-sized band 30. For example, the band 30 may have a first end that is separated from a second end. In such an example, the first end may have two or more holes that extend along the first end at different locations, and the second end may have a buckle or peg configured to fit into one of the holes. As such, the user may adjust the length of the band 30 by selecting a particular hole to fit the buckle or peg into. In particular embodiments, adjusting the size of the band 30 may increase or decrease the amount of pressure applied to one or more pressure points by the acupressure device 14. The band 30 may be formed (or otherwise be made) from any material. For example, the band 30 may be rubber, latex, latex-free rubber, plastic, a polymer (such as a synthetic polymer, a semi-synthetic polymer, or a natural polymer), a ceramic, glass, metal, an aroma-permeable material, any other material, or any combination of the preceding. In particular embodiments, the band 30 may be any material capable of absorbing, binding, or retaining (in some manner) an amount of therapeutic substance 18. In particular embodiments, the band 30 may be formed from two or more of the above-listed materials. In particular embodiments, the band 30 may be a thermoplastic vulcanite injected moldable latex-free rubber band. The band 30 may have any size (e.g., length, width, thickness, etc.), and the size may vary based on the mammal for which the band 30 is designed. For example, the size of the band 30 may be larger for an adult human than for a child human. As another example, the size of the band 30 may be larger for a horse than for a dog. Example sizes of band 30 are listed below.

The band 30 includes an exterior portion 34 and an interior portion 38. The exterior portion 34 is configured to face away from the wrist (or appendage) of the mammal when the band 30 is worn by the mammal. The exterior portion 34 of the band 30 may include one or more graphics and/or one or more decorations. The interior portion 38 is configured to face towards the wrist (or appendage) of the mammal when the band 30 is worn by the mammal.

The acupressure device 14 further includes one or more raised elements 42 that may be configured to apply pressure to the one or more pressure points on the mammal (or at a location substantially positioned at one or more pressure points on the mammal). A raised element 42 may be configured to apply pressure to any one or more pressure points described above with regard to FIG. 1. For example, a raised element 42 may be configured to apply pressure to the P6 pressure point of an adult human. As illustrated, the raised element 42 is positioned on the interior portion 38 of the band 30. As such, when the acupressure device 14 is worn by the mammal, the raised element 42 may apply pressure to a pressure point on the mammal, such as, for example, the P6 pressure point. In such an example, the pressure applied by the raised element 42 may assert a frequency (such as a 0.5 Hz frequency) to, for example, the median nerve, thereby generating anti-nausea hormones to provide nausea relief, for example. In particular embodiments, the raised element 42 may be configured to vibrate and/or resonate. For example, the raised element 42 may include a vibration and/or resonation source that vibrates and/or resonates when an electrical current is provided to the source. The raised element 42 may vibrate and/or resonate at any frequency.

The acupressure device 14 may include any number of raised elements 42, such as one, two, three, four, five, or any other number of raised elements 42. A raised element 42 may be formed as a part of the material of the band 30, may be one or more inserts that may be temporarily attached to the band 30, or may be fixedly (and/or permanently) attached to the band 30. As illustrated, the raised element 42 is formed as a part of the material of the band 30. The raised element 42 may be formed (or otherwise be made) from any material. For example, the raised element 42 may be rubber, latex, latex-free rubber, plastic, a polymer (such as a synthetic polymer, a semi-synthetic polymer, or a natural polymer), a ceramic, glass, metal, an aroma-permeable material, any other material, or any combination of the preceding. The raised element 42 may be formed from the same material as the band 30, or from a different material. The raised element 42 may have any shape for applying pressure to a pressure point. For example, the raised element 42 may be rectangular, pin-shaped, shaped-like a ridge in the band 30, oval shaped, spherical shape, semi-spherical shape, any other shape, or any combination of the preceding. As illustrated, the raised element 42 is oval shaped (or egg shaped). The raised element 42 may have any size. Example sizes of the raised element 42 are listed below.

As is discussed above with regard to FIG. 1, one or more therapeutic substances 18 (not shown in FIGS. 3a-3b) may be coupled to acupressure device 14. The therapeutic substances 18 may include any one or more therapeutic substances 18 discussed above with regard to FIG. 1. As one example, the therapeutic substance 18 may be an essential oil derived from a peppermint plant (e.g., a peppermint essential oil). The therapeutic substance 18 may be coupled to the acupressure device 14 in any manner discussed above with regard to FIG. 1. As one example, the therapeutic substance 18 may be infused into the acupressure device 14. The therapeutic substance 18 may be coupled to all or a portion of the acupressure device 14. For example, the therapeutic substance 18 may be coupled to all (or a portion) of the exterior portion 34 of the band 30, all (or a portion) of the interior portion 38 of the band, all or a portion of the raised element 42, or any combination of the preceding.

As is discussed above, the band 30 and/or the raised element 42 of the acupressure device 14 may have any size. An example of such sizes may include the following illustrated in FIG. 3a:
A=25.00 mm
B=radius of 35.00 mm
C=7.50 mm
D=15.00 mm
E=0.50 mm
F=radius of 0.50 mm
G=radius of 5.50 mm
H=7.50 mm
I=Ø of 13.20 mm
J=9.00 mm
K=Ø of 54.44 mm
L=radius of 25.00 mm Another example of such sizes may include the following illustrated in FIG. 3b:
AA=0.394 inches
BB=0.354 inches
CC=0.12 inches
DD=radius of 0.16 inches
EE=0.572 inches
FF=radius of 0.787 inches
GG=Ø of 1.752 inches
HH=Ø of 0.394 inches
II=0.236 inches
JJ=radius of 0.020 inches
KK=0.472 inches Although the band 30 and the raised element 42 have been illustrated as including particular sizes, the band 30 and/or raised element 42 (or any other acupressure device 14) may have any other size.

Modifications, additions, or omissions may be made to the acupressure device 14 without departing from the scope of the invention. For example, although the acupressure device 14 is illustrated as a wrist band (or an appendage band), the acupressure device 14 may be any other acupressure device, as is discussed above with regard to FIG. 1.

Figure 3C:
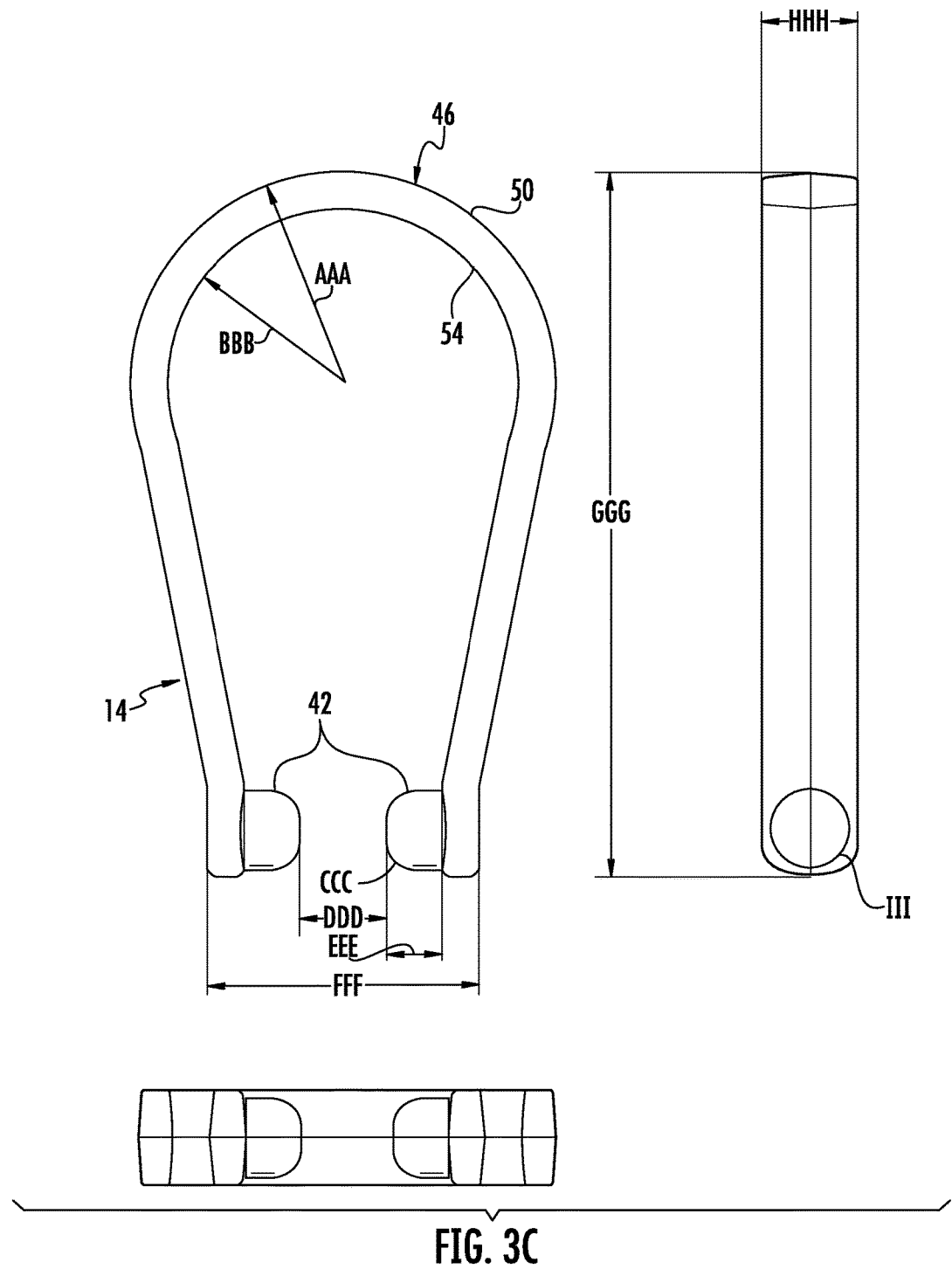

FIG. 3c illustrates another example of an acupressure device of FIG. 1. As illustrated, the acupressure device 14 may be a hand clip that may be worn by a mammal (such as an adult human, a child human, a monkey, or any other mammal) on the mammal's hand.

According to the illustrated embodiment, the acupressure device 14 includes a clip portion 46. The clip portion 46 is configured to be placed in the wedge between a person's fingers. The clip portion 46 may be formed (or otherwise be made) from any material. For example, the clip portion 46 may be rubber, latex, latex-free rubber, plastic, a polymer (such as a synthetic polymer, a semi-synthetic polymer, or a natural polymer), a ceramic, glass, metal, an aroma-permeable material, any other material, or any combination of the preceding. In particular embodiments, the clip portion 46 may be any material capable of absorbing, binding, or retaining (in some manner) an amount of therapeutic substance 18. In particular embodiments, the clip portion 46 may be formed from two or more of the above-listed materials. In particular embodiments, the clip portion 46 may be a thermoplastic vulcanite injected moldable latex-free rubber clip. The clip portion 46 may have any size (e.g., length, width, thickness, etc.), and the size may vary based on the mammal for which the clip portion 46 is designed. For example, the size of the clip portion 46 may be larger for an adult human than for a child human. Example sizes of clip portion 46 are listed below.

The clip portion 46 includes an exterior portion 50 and an interior portion 54. The exterior portion 50 is configured to face away from the hand of the mammal when the clip portion 46 is worn by the mammal. The exterior portion 50 of the clip portion 46 may include one or more graphics and/or one or more decorations. The interior portion 54 is configured to face towards the hand of the mammal when the clip portion 46 is worn by the mammal.

The acupressure device 14 further includes one or more raised elements 42 that may be configured to apply pressure to the one or more pressure points on the mammal (or at a location substantially positioned at one or more pressure points on the mammal). A raised element 42 may be configured to apply pressure to any one or more pressure points described above with regard to FIG. 1. For example, a raised element 42 may be configured to apply pressure to the LI4 pressure point of an adult human. As illustrated, the raised element 42 is positioned on the interior portion 54 of the clip portion 46. As such, when the acupressure device 14 is worn by the mammal, the raised element 42 may apply pressure to a pressure point on the mammal, such as, for example, the LI4 pressure point. In particular embodiments, the raised element 42 may be configured to vibrate and/or resonate. For example, the raised element 42 may include a vibration and/or resonation source that vibrates and/or resonates when an electrical current is provided to the source. The raised element 42 may vibrate and/or resonate at any frequency.

The acupressure device 14 may include any number of raised elements 42, such as one, two, three, four, five, or any other number of raised elements 42. A raised element 42 may be formed as a part of the material of the clip portion 46, may be one or more inserts that may be temporarily attached to the clip portion 46, or may be fixedly (and/or permanently) attached to the clip portion 46. As illustrated, the raised elements 42 are formed as a part of the material of the clip portion 46. The raised element 42 may be formed (or otherwise be made) from any material. For example, the raised element 42 may be rubber, latex, latex-free rubber, plastic, a polymer (such as a synthetic polymer, a semi-synthetic polymer, or a natural polymer), a ceramic, glass, metal, an aroma-permeable material, any other material, or any combination of the preceding. The raised element 42 may be formed from the same material as the clip portion 46, or from a different material. The raised element 42 may have any shape for applying pressure to a pressure point. For example, the raised element 42 may be rectangular, pin-shaped, shaped-like a ridge in the clip portion 46, oval shaped, spherical shape, semi-spherical shape, any other shape, or any combination of the preceding. As illustrated, the raised element 42 is oval shaped (or egg shaped). The raised element 42 may have any size. Example sizes of the raised element 42 are listed below.

As is discussed above with regard to FIG. 1, one or more therapeutic substances 18 (not shown in FIG. 3c) may be coupled to acupressure device 14. The therapeutic substances 18 may include any one or more therapeutic substances 18 discussed above with regard to FIG. 1. As one example, the therapeutic substance 18 may be an essential oil derived from a peppermint plant (e.g., a peppermint essential oil). The therapeutic substance 18 may be coupled to the acupressure device 14 in any manner discussed above with regard to FIG. 1. As one example, the therapeutic substance 18 may be infused into the acupressure device 14. The therapeutic substance 18 may be coupled to all or a portion of the acupressure device 14. For example, the therapeutic substance 18 may be coupled to all (or a portion) of the exterior portion 50 of the clip portion 46, all (or a portion) of the interior portion 54 of the clip portion 46, all or a portion of the raised element 42, or any combination of the preceding.

As is discussed above, the clip portion 46 and/or the raised element 42 of the acupressure device 14 may have any size. An example of such sizes may include the following illustrated in FIG. 3c:

AAA=radius of 30.00 mm
BBB=radius of 25.00 mm
CCC=radius 4.49 mm
DDD=13.00 mm
EEE=7.95 mm
FFF=39.60 mm
GGG=101.98 mm
HHH=14.00 mm
III=radius of 5.75 mm Although the clip portion 46 and the raised element 42 have been illustrated as including particular sizes, the clip portion 46 and/or raised element 42 (or any other acupressure device 14) may have any other size.

Modifications, additions, or omissions may be made to the acupressure device 14 without departing from the scope of the invention. For example, although the acupressure device 14 is illustrated as a hand clip, the acupressure device 14 may be any other acupressure device, as is discussed above with regard to FIG. 1.

Figure 3D:
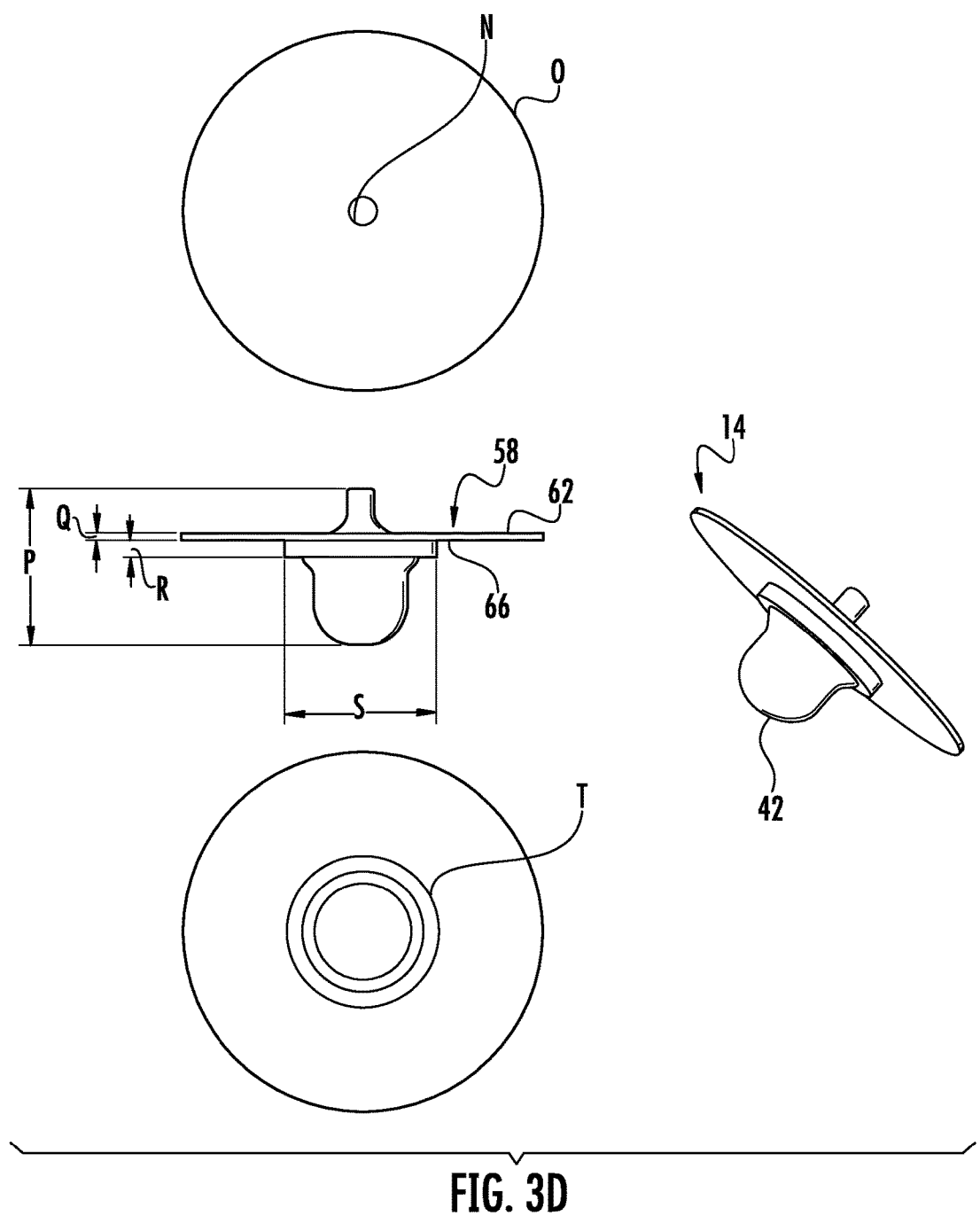

FIG. 3d illustrates another example of an acupressure device of FIG. 1. As illustrated, the acupressure device 14 may be a sticker (or patch) that may be worn by a mammal (such as an adult human, a child human, a dog, a cat, a horse, or any other mammal) on any area of the mammal's body.

According to the illustrated embodiment, the acupressure device 14 includes an adhesive portion 58. The adhesive portion 58 is configured to be placed on any area of the mammal's body (such as the mammal's back or forehead), and further configured to adhere to the mammal's body. The adhesive portion 58 may be formed (or otherwise be made) from any material. For example, the adhesive portion 58 may be rubber, latex, latex-free rubber, plastic, a polymer (such as a synthetic polymer, a semi-synthetic polymer, or a natural polymer), a ceramic, glass, metal, an aroma-permeable material, any other material, or any combination of the preceding. In particular embodiments, the adhesive portion 58 may be any material capable of absorbing, binding, or retaining (in some manner) an amount of therapeutic substance 18. In particular embodiments, the adhesive portion 58 may be formed from two or more of the above-listed materials. In particular embodiments, the adhesive portion 58 may be a thermoplastic vulcanite injected moldable latex-free rubber portion. The adhesive portion 58 may have any size (e.g., length, width, thickness, etc.), and the size may vary based on the mammal for which the adhesive portion 58 is designed. For example, the size of the adhesive portion 58 may be larger for an adult human than for a child human. Example sizes of adhesive portion 58 are listed below.

The adhesive portion 58 includes an exterior portion 62 and an interior portion 66. The exterior portion 62 is configured to face away from the area of the mammal to which it is adhered. The exterior portion 62 of the adhesive portion 58 may include one or more graphics and/or one or more decorations. Furthermore, the exterior portion 62 may include a placement stem that may allow the user to position the acupressure device 14 on a location on the mammal's body, and to remove the acupressure device. The interior portion 66 is configured to face the area of the mammal to which it is adhered. Furthermore, the interior portion 66 is further configured to adhere to the body of the mammal. The interior portion 66 may include any type of adhering substance (or structure) allowing it to adhere to the body. For example, the interior portion 66 may include an adhesive tape, an adhesive glue, a structural adhesive, a pressure sensitive adhesive, any other adhering substance (or structure) that allows the acupressure device to adhere to the body of a mammal, or any combination of the preceding. In particular embodiments, the adhesive substance (or structure) may allow the adhesive portion 58 to be removed from one area of the mammal's body, and re-adhered to another area of the mammal's body.

The acupressure device 14 further includes one or more raised elements 42 that may be configured to apply pressure to the one or more pressure points on the mammal (or at a location substantially positioned at one or more pressure points on the mammal). A raised element 42 may be configured to apply pressure to any one or more pressure points described above with regard to FIG. 1. For example, a raised element 42 may be configured to apply pressure to the B2 pressure point of an adult human. As illustrated, the raised element 42 is positioned on the interior portion 66 of the adhesive portion 62. As such, when the acupressure device 14 is worn by the mammal (or otherwise adhered to the body of the mammal), the raised element 42 may apply pressure to a pressure point on the mammal, such as, for example, the B2 pressure point. In particular embodiments, the raised element 42 may be configured to vibrate and/or resonate. For example, the raised element 42 may include a vibration and/or resonation source that vibrates and/or resonates when an electrical current is provided to the source. The raised element 42 may vibrate and/or resonate at any frequency.

The acupressure device 14 may include any number of raised elements 42, such as one, two, three, four, five, or any other number of raised elements 42. A raised element 42 may be formed as a part of the material of the adhesive portion 62, may be one or more inserts that may be temporarily attached to the adhesive portion 62, or may be fixedly (and/or permanently) attached to the adhesive portion 62. As illustrated, the raised elements 42 are formed as a part of the material of the adhesive portion 62. The raised element 42 may be formed (or otherwise be made) from any material. For example, the raised element 42 may be rubber, latex, latex-free rubber, plastic, a polymer (such as a synthetic polymer, a semi-synthetic polymer, or a natural polymer), a ceramic, glass, metal, an aroma-permeable material, any other material, or any combination of the preceding. The raised element 42 may be formed from the same material as the adhesive portion 62, or from a different material. The raised element 42 may have any shape for applying pressure to a pressure point. For example, the raised element 42 may be rectangular, pin-shaped, shaped-like a ridge in the clip portion 46, oval shaped, spherical shape, semi-spherical shape, any other shape, or any combination of the preceding. As illustrated, the raised element 42 is oval shaped (or egg shaped). The raised element 42 may have any size. Example sizes of the raised element 42 are listed below.

As is discussed above with regard to FIG. 1, one or more therapeutic substances 18 (not shown in FIG. 3*d*) may be coupled to acupressure device 14. The therapeutic substances 18 may include any one or more therapeutic substances 18 discussed above with regard to FIG. 1. As one example, the therapeutic substance 18 may be an essential oil derived from a *eucalyptus* plant (e.g., an *eucalyptus* essential oil). The therapeutic substance 18 may be coupled to the acupressure device 14 in any manner discussed above with regard to FIG. 1. As one example, the therapeutic substance 18 may be infused into the acupressure device 14. The therapeutic substance 18 may be coupled to all or a portion of the acupressure device 14. For example, the therapeutic substance 18 may be coupled to all (or a portion) of the exterior portion 62 of the adhesive portion 58, all (or a portion) of the interior portion 66 of the adhesive portion 58, all or a portion of the raised element 42, or any combination of the preceding.

As is discussed above, the adhesive portion 58 and/or the raised element 42 of the acupressure device 14 may have any size. An example of such sizes may include the following illustrated in FIG. 3*c*:

N=Ø of 3.00 mm
O=Ø of 38.15 mm
P=16.50 mm
Q=0.70 mm
R=1.80 mm
S=16.00 mm
T=Ø of 16.00 mm

Although the adhesive portion 58 and the raised element 42 have been illustrated as including particular sizes, the adhesive portion 58 and/or raised element 42 (or any other acupressure device 14) may have any other size.

Modifications, additions, or omissions may be made to the acupressure device 14 without departing from the scope of the invention. For example, although the acupressure device 14 is illustrated as a sticker (or patch), the acupressure device 14 may be any other acupressure device, as is discussed above with regard to FIG. 1.

FIG. 3*e* illustrates a further example of an acupressure device of FIG. 1. As illustrated, the acupressure device 14 may be a head band that may be worn by a mammal (such as an adult human, a child human, a dog, a cat, a horse, or any other mammal) on (or around) the mammal's head.

According to the illustrated embodiment, the acupressure device 14 includes a band 70. The band 70 is configured to encircle the head of the mammal (such as an adult human). In particular embodiments, the band 70 may be further configured to be positioned so as to be in direct or indirect contact with the back of the neck of the mammal (in addition to being in contact with a portion of the head of the mammal). As such, the acupressure device 14 may apply pressure to one or more pressure points in the head of the mammal (such as, for example, TW23) and/or in the back of the neck of the mammal (such as, for example, GB20), in particular embodiments. As illustrated, the band 70 is an adjustable-sized band 70. For example, the band 70 may have a first end that is separated from a second end. In such an example, the first end may have two or more holes that extend along the first end at different locations, and the second end may have a buckle or peg configured to fit into one of the holes. As such, the user may adjust the length of the band 70 by selecting a particular hole to fit the buckle or peg into. In particular embodiments, adjusting the size of the band 70 may increase or decrease the amount of pressure applied to one or more pressure points by the acupressure device 14. In particular embodiments, the band 70 may be a continuous loop. In such an embodiment, the band 70 may be a single size band that may be flexible so as to expand (at least partially) to fit various sized mammals. The band 70 may be formed (or otherwise be made) from any material. For example, the band 70 may be rubber, latex, latex-free rubber, plastic, a polymer (such as a synthetic polymer, a semi-synthetic polymer, or a natural polymer), a ceramic, glass, metal, an aroma-permeable material, any other material, or any combination of the preceding. In particular embodiments, the band 70 may be any material capable of absorbing, binding, or retaining (in some manner) an amount of therapeutic substance 18. In particular embodiments, the band 70 may be formed from two or more of the above-listed materials. In particular embodiments, the band 70 may be a thermoplastic vulcanite injected moldable latex-free rubber band. The band 70 may have any size (e.g., length, width, thickness, etc.), and the size may vary based on the mammal for which the band 70 is designed. For example, the size of the band 70 may be larger for an adult human than for a child human. As another example, the size of the band 70 may be larger for a horse than for a dog. Example sizes of band 70 are listed below.

The band 70 includes an exterior portion 74 and an interior portion 78. The exterior portion 74 is configured to face away from the head of the mammal when the band 70 is worn by the mammal. The exterior portion 74 of the band 70 may include one or more graphics and/or one or more decorations. The interior portion 78 is configured to face towards the head of the mammal when the band 70 is worn by the mammal.

The acupressure device 14 further includes one or more raised elements 42 that may be configured to apply pressure to the one or more pressure points on the mammal (or at a location substantially positioned at one or more pressure points on the mammal). A raised element 42 may be configured to apply pressure to any one or more pressure points described above with regard to FIG. 1. For example, a raised element 42 may be configured to apply pressure to the B2 pressure point of an adult human. As illustrated, the raised element 42 is positioned on the interior portion 78 of the band 70. As such, when the acupressure device 14 is worn by the mammal, the raised element 42 may apply pressure to a pressure point on the mammal, such as, for example, the B2 pressure point. In particular embodiments, the raised element 42 may be configured to vibrate and/or resonate. For example, the raised element 42 may include a vibration and/or resonation source that vibrates and/or resonates when an electrical current is provided to the source. The raised element 42 may vibrate and/or resonate at any frequency.

The acupressure device 14 may include any number of raised elements 42, such as one, two, three, four, five, or any other number of raised elements 42. A raised element 42 may be formed as a part of the material of the band 70, may be one or more inserts that may be temporarily attached to the band 70, or may be fixedly (and/or permanently) attached to the band 70. As illustrated, the raised element 42 is an insert that may be temporarily attached to the band 70. For example, the band 70 includes one or more holes that may receive and hold the raised element 42. The band 70 may include any number of holes, such as one, two, three, four, five, or any other number of raised elements 42. In particular embodiments, the user may choose to insert one or more raised elements 42 into one or more of the holes in band 70 so that the raised elements 42 apply pressure to particular pressure points. For example, the user may choose to insert the raised elements 42 in a first set of one or more holes in order to apply pressure to the B2 pressure points of the mammal, and/or to insert the raised elements 42 into a second set of one or more holes in order to apply pressure to the TW23 pressure points of the mammal.

The raised element 42 may be formed (or otherwise be made) from any material. For example, the raised element 42 may be rubber, latex, latex-free rubber, plastic, a polymer (such as a synthetic polymer, a semi-synthetic polymer, or a natural polymer), a ceramic, glass, metal, an aroma-permeable material, any other material, or any combination of the preceding. The raised element 42 may be formed from the same material as the band 70, or from a different material. The raised element 42 may have any shape for applying pressure to a pressure point. For example, the raised element 42 may be rectangular, pin-shaped, shaped-like a ridge in the band 70, oval shaped, spherical shape, semi-spherical shape, any other shape, or any combination of the preceding. As illustrated, the raised element 42 is oval shaped (or egg shaped). The raised element 42 may have any size. Example sizes of the raised element 42 are listed below.

As is discussed above with regard to FIG. 1, one or more therapeutic substances 18 (not shown in FIG. 3e) may be coupled to acupressure device 14. The therapeutic substances 18 may include any one or more therapeutic substances 18 discussed above with regard to FIG. 1. As one example, the therapeutic substance 18 may be an essential oil derived from an *eucalyptus* plant (e.g., an *eucalyptus* essential oil). The therapeutic substance 18 may be coupled to the acupressure device 14 in any manner discussed above with regard to FIG. 1. As one example, the therapeutic substance 18 may be infused into the acupressure device 14. The therapeutic substance 18 may be coupled to all or a portion of the acupressure device 14. For example, the therapeutic substance 18 may be coupled to all (or a portion) of the exterior portion 74 of the band 70, all (or a portion) of the interior portion 78 of the band 70, all or a portion of the raised element 42, or any combination of the preceding.

As is discussed above, the band 70 and/or the raised element 42 of the acupressure device 14 may have any size. An example of such sizes may include the following illustrated in FIG. 3e:

NN=25.00 mm
OO=12.50 mm
PP=5.00 mm
QQ=765.00 mm
RR=16.50 mm
SS=1.50 mm
TT=9.00 mm

Although the band 70 and the raised element 42 have been illustrated as including particular sizes, the band 70 and/or raised element 42 (or any other acupressure device 14) may have any other size.

Modifications, additions, or omissions may be made to the acupressure device 14 without departing from the scope of the invention. For example, although the acupressure device 14 is illustrated as a head band, the acupressure device 14 may be any other acupressure device, as is discussed above with regard to FIG. 1.

Figure 4:
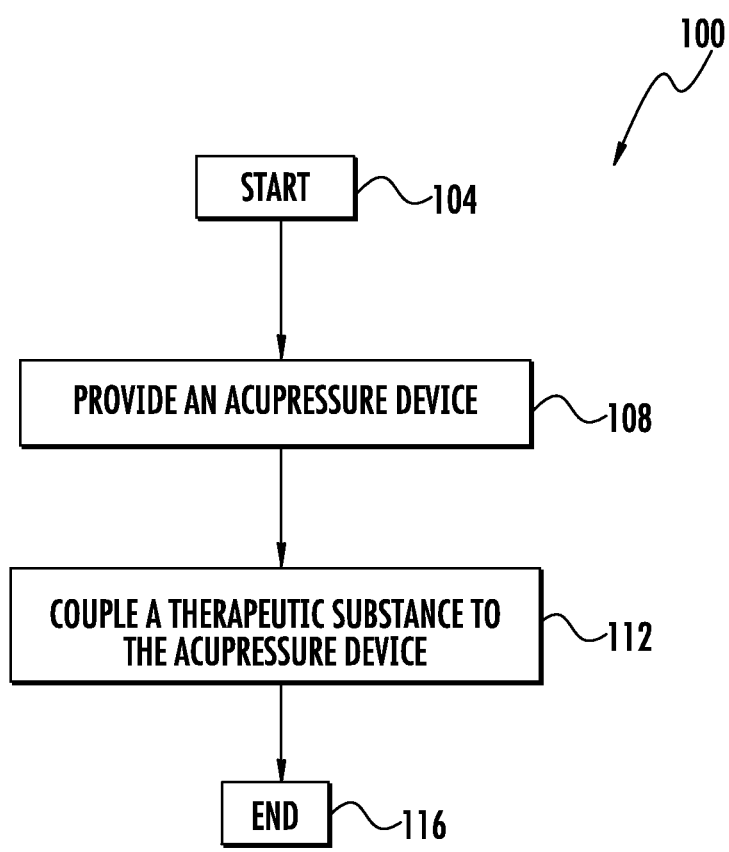
FIG. 4 illustrates an example method of providing a therapeutic substance and acupressure system.

FIG. 4 illustrates an example method of providing a therapeutic substance and acupressure system. The steps of method 100 may be performed by any one or more entities. For example, the steps of method 100 may be performed by a manufacturer of an acupressure device, a reseller (or modifier or enhancer) of an acupressure device, a customer that purchases the acupressure device, any other entity, or any combination of the preceding.

The method begins at step 104. At step 108, an acupressure device 14 is provided. The acupressure device 14 may be any of the acupressure devices 14 discussed above with regard to FIGS. 1 and 3. For example, the acupressure device 14 may be a wrist band configured to apply pressure to a P6 pressure point of an adult human. The acupressure device 14 may be configured to provide pressure on any one or more pressure points of a mammal, as is also discussed above with regard to FIGS. 1 and 3. The acupressure device 14 may be provided in any manner. For example, the acupressure device 14 may be provided by manufacturing (or otherwise forming) the acupressure device 14. As another example, the acupressure device 14 may be provided by purchasing (or otherwise obtaining) all or a portion of the acupressure device 14.

At step 112, a therapeutic substance 18 is coupled to the acupressure device 14. The therapeutic substance 18 may be any one or more of the therapeutic substances 18 discussed above with regard to FIGS. 1 and 3. For example, the therapeutic substance 18 may be an essential oil derived from a peppermint plant (e.g., a peppermint essential oil). The therapeutic substance 18 may be coupled to the acupressure device 14 in any of the manners discussed above with regard to FIGS. 1 and 3. For example, the acupressure device 14 may be infused with the therapeutic substance 18. As other examples, the therapeutic substance 18 may incorporated into the acupressure device 14 during the manufacturing process, topically applied to the acupressure device 14, provided as a coating on the acupressure device 14, sprayed onto the acupressure device 14, positioned within a container in the acupressure device 14, coupled to the acupressure device 14 in any other manner, or any combination of the preceding. Additionally, coupling the therapeutic substance 18 to the acupressure device 14 may refer to coupling the therapeutic substance 18 to all or a portion of the acupressure device 14 (such as all or a portion of the band 30, exterior portion 34, interior portion 38, raised element 42, or any combination of the preceding). Furthermore, any number of therapeutic substances 18 may be coupled to the acupressure device 14, such as one, two, three, four, five, ten, or any other number of therapeutic substances 18. After the therapeutic substance 18 has been coupled to the acupressure device 14, the method 100 may move to step 116, where the method 100 ends.

Modifications, additions, or omissions may be made to method 100. Additionally, the steps of method 100 may be performed in parallel or in any suitable order. For example, the therapeutic substance 18 may be coupled to the acupressure device 14 at the same time (or substantially the same time) as when the acupressure device 14 is provided, such as when the therapeutic substance 18 is coupled to the acupressure device 14 during manufacturing and/or packaging of the acupressure device 14.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification. In this manner, Applicant reserves the right to amend the claims during prosecution to add features as variously described in this specification, and such amendments comply with the requirements of 35 U.S.C. §§ 112(a) and 132(a).

The invention claimed is:

1. A system, comprising:
an acupressure device comprising a single sized continuous loop latex-free rubber wrist band formed of thermoplastic vulcanizate (TPV), the single sized continuous loop latex-free rubber wrist band having a raised element positioned on an interior portion of the single sized continuous loop latex-free rubber wrist band, the raised element applying pressure to a specific pressure point at or near a wrist of a mammal when the single sized continuous loop latex-free rubber wrist band encircles the wrist of the mammal; and
a therapeutic substance mixed into the TPV of the single sized continuous loop latex-free rubber wrist band, wherein the therapeutic substance is an aromatic essential oil that is mixed into the TPV of the single sized continuous loop latex-free rubber wrist band at a concentration of 0.5% to 20% of the weight basis of the single sized continuous loop latex-free rubber wrist band having the therapeutic substance, wherein the aromatic essential oil emits an aroma for inhalation by the mammal to provide an aromatherapy effect.

2. The system of claim 1, wherein the aromatic essential oil is derived from a plant selected from a group consisting of: basil, bay, benzoin, birch, buchu, cajeput, calamus, camphor, *cannabis sativa*, caraway, carrot seed, citronella, clove, coriander, cumin, cypress, dill, *eucalyptus, eucalyptus* lemon, *eucalyptus* peppermint, *eucalyptus radiate*, evening primrose, fennel, frankincense, galbanum, geranium, ginger, grapefruit, hyssop, jasmine, juniper, lavender, lemon, lemon grass, lime, mandarin orange, melaleuca, mustard, myrrh, myrtle, nutmeg, orange, oregano, palma rose, parsley, patchouli, peppermint, perilla, pimento, pine, rose, rosehip, rosemary, rosewood, sage, sandalwood, spearmint, tagetes, tangerine, tarragon, tea tree, thyme, thyme red, valerian, and wintergreen.

3. The system of claim 1, wherein the specific pressure point at or near the wrist of the mammal is selected from a group consisting of: P6, LI4, L8, H7, PC2-PC9, TH1-TH14, LU3-LU11, TW5, LI11, LI2, LI3, LI7, LI14, L14, LI5, LI8, LI10, LI12, LI13, P3, P7, HT7, and LI1.

4. The system of claim 1, wherein the specific pressure point at or near the wrist of the mammal is the P6 pressure point, and wherein the aromatic essential oil is derived from a peppermint plant.

5. The system of claim 1, wherein the specific pressure point at or near the wrist of the mammal is the H7 pressure point or the HT7 pressure point, and wherein the aromatic essential oil is derived from a lavender plant.

6. The system of claim 1, wherein the raised element asserts a 0.5 Hz frequency to a median nerve of the mammal when the single sized continuous loop latex-free rubber wrist band encircles the wrist of the mammal.

7. The system of claim 1, wherein the single sized continuous loop latex-free rubber wrist band is configured to stretch.

8. The system of claim 1, wherein the raised element applies pressure to a K6 pressure point, a K3 pressure point, or a SP6 pressure point of the mammal when the single sized continuous loop latex-free rubber wrist band encircles a leg or foot of the mammal.

* * * * *